United States Patent
Iacono et al.

(10) Patent No.: US 10,385,077 B1
(45) Date of Patent: Aug. 20, 2019

(54) FLUORINATED CYCLOALKENE FUNCTIONALIZED SILICAS

(71) Applicant: The United States as Represented by the Secretary of the Air Force, Wright-Patterson AFB, OH (US)

(72) Inventors: Scott Iacono, Colorado Springs, CO (US); Abby Rose Jennings, Colorado Springs, CO (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 16/269,583

(22) Filed: Feb. 7, 2019

Related U.S. Application Data

(60) Division of application No. 15/587,819, filed on May 5, 2017, now Pat. No. 10,253,050, which is a continuation of application No. 15/074,128, filed on Mar. 8, 2016, now Pat. No. 9,695,203.

(60) Provisional application No. 62/138,759, filed on Mar. 26, 2015, provisional application No. 62/241,454, filed on Oct. 14, 2015.

(51) Int. Cl.
*C07F 7/18* (2006.01)
*B01J 31/28* (2006.01)

(52) U.S. Cl.
CPC ............. *C07F 7/1876* (2013.01); *B01J 31/28* (2013.01); *B01J 2231/323* (2013.01); *B01J 2531/828* (2013.01)

(58) Field of Classification Search
None
See application file for complete search history.

(56) References Cited

U.S. PATENT DOCUMENTS

| 4,990,633 | A | 2/1991 | Negele et al. |
| 5,932,760 | A | 8/1999 | Lui et al. |
| 2012/0148808 | A1* | 6/2012 | Kubota ............... C08F 220/18 428/195.1 |

OTHER PUBLICATIONS

"Anomalous Macromolecular Assembly of Partially Fluorinated Polyhedral Oligomeric Silsesquioxanes," Kettwich, S. C.; Pierson, S. N.; Peloquin, A. J.; Mabry, J. M.; Iacono, S. T. New J. Chem. 2012, 36, 941. (6 Pages).

"Ultrahydrophobic Fluorinated Polyhedral Oligomeric Silsesquioxanes (F-POSS)," Mabry, J. M.; Vij, A.; Iacono, S. T.; Viers, B. M. Angew. Chem. Int. Ed. 2008, 22, 4137. (4 Pages).

"Facile Synthesis of Hydrophobic Fluoroalkyl Functionalized Silsesquioxane Nanostructures," Iacono, S. T.; Grabow, W.; Ashwani, V.; Smith, D. W., Jr.; Mabry, J. M. Chem. Commun. 2007, 47, 4992. (4 Pages).

"Polyfluorinated Compounds: Past, Present, and Future," Lindstrom, A.B.; Strynar, M.J.; Libelo, E.L., Environ. Sci. Technol., 2011, 45, 7954-7961. (8 pages).

"Development of Fluorocyclic Precursors for Organically Modified Silica Materials and Composites," Jennings, A.R.; Thrasher, C.J.; and Iacono, S.T.; Abstract for Fluoropolymer Meeting, which was held in San Diego, CA on Oct. 13-16, 2014. (1 Page).

"Development of Fluorocyclic Precursors for Organically Modified Silica Materials and Composites," Jennings, A.R.; Thrasher, C.J.; and Iacono, S.T.; Poster presented at Fluoropolymer Meeting on Oct. 14, 2014. (1 Page).

Sharma, Ultra low dielectric, self-cleansing and highly oleophobic POSS-PFCP aryl ether polymer composites, J. Mater. Chem. C, 2013, 1, 7222.

\* cited by examiner

*Primary Examiner* — Clinton A Brooks
*Assistant Examiner* — Kofi Adzamli
(74) *Attorney, Agent, or Firm* — AFMCLO/JAZ; Timothy Barlow

(57) ABSTRACT

Fluorinated cyclopentene moieties and fluorinated cyclopentene functionalized silica materials are provided. The fluorinated cyclopentene functionalized silica materials include a silica material having the fluorinated cyclopentene moiety covalently bonded thereto. Exemplary silica materials include a polysilsesquioxane, a nanosilica, a microsilica, a silica gel, a silica aerogel, or combinations thereof. The fluorinated cyclopentene moieties are based on a modification of perfluorocyclopentene (i.e., 1,2,3,3,4,4,5,5-octafluoro-1-cyclopentene) by nucleophilic substitution with an appropriate nucleophile having a reactive functional group. Methods for preparing fluorinated cyclopentene moieties and the corresponding fluorinated cyclopentene functionalized silica materials are also provided.

5 Claims, 9 Drawing Sheets

Formula [1]

| | $R^1$ |
|---|---|
| 1. | Propenyl |
| 2. | Propynyl |
| 3. | Butenyl |
| 4. | Butynyl |
| 5. | Eugenyl |
| 6. | Propenyl |
| 7. | Eugenyl |

Exemplary

Formula [2]

| | $R^2$ |
|---|---|
| | Propenyl |
| | Propynyl |
| | Butenyl |
| | Butynyl |
| | Eugenyl |
| | hexafluoro-2-propanol |
| | hexafluoro-2-propanol |

FLUORINATED CYCLOALKENE FUNCTIONALIZED SILICAS

CROSS-REFERENCE TO RELATED APPLICATIONS

The present application claims the benefit of and priority to U.S. Non-Provisional application Ser. No. 15/587,819, filed May 5, 2017, which claims priority from U.S. Non-Provisional application Ser. No. 15/074,128, filed Mar. 18, 2016, which claims priority from U.S. Provisional Patent Application Ser. Nos. 62/138,759, filed Mar. 26, 2015, and 62/241,454, filed Oct. 14, 2015, each of which is hereby incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to the synthesis of substituted fluorinated cycloalkane moieties and the use of same in the preparation of fluorinated organic modified silica materials.

BACKGROUND OF THE INVENTION

Fluorinated materials have been readily integrated into polymers, composites, and other functional materials for use in a wide range of applications, such as non-wetting, low-surface energy coatings. The use of fluorinated organic modified silicas over more conventional low-surface energy components, such as polytetrafluoroethylene, have shown to be advantageous due to the improvement in the fluorinated materials' mechanical strength and durability. Types of fluorinated organic molecular and network silicas that have been employed for such purposes include polysilsesquioxanes, such as polyoctahedralsilsequioxanes ("POSS"), micro/nanometer-sized silica particles (e.g., microsilicas or nanosilicas), silica gels, and high surface area silica aerogels.

In addition to the improvement in mechanical properties, fluorinated organic modified silicas are highly desirable because of the unique combination of thermal stability, chemical resistance, low surface energy, low refractive index, and high insulating ability. Furthermore, as nanometer-sized materials, these fluorinated organic modified silicas are compatible as fillers with organic polymers as the host matrix and can influence properties of organic systems making them highly attractive for the development of high performance, hybrid organic-inorganic materials.

Previous efforts to obtain fluorinated organic modified silicas have relied heavily on incorporating perfluorinated carbon chains into the periphery of the materials' structure. Due to a heightened concern over the environmental impacts of perfluorinated carbon chains, there is growing need for alternatives that mitigate these fears whilst maintaining the desired properties.

One conventional avenue for circumventing use of perfluorinated carbon chains is the implementation of fluorocyclic compounds, such as perfluorocylcobutane ("PFCB") and perfluorocyclopentene ("PFCP"), especially in those silicas exceeding four continuous perfluorocarbon chains (e.g., $\geq C_6$). The use of PFCB is becoming less common due to a number of factors, mainly because of the limited commercial-availability of the monomer derived from Halon 2402 (R-114B2, a fire suppressant), which has been banned by the U.S. under the Clean Air Act ("CAA") since Jan. 1, 1994. Recycled Halon 2402 and inventories produced before Jan. 1, 1994 are now the only sources, and supply is limited. Additionally, the cost effectiveness and number of steps of the overall synthesis in obtaining monomers for PFCB containing materials continue to limit its production.

In contrast, PFCP is readily available and is highly reactive towards nucleophiles, allowing for a wide variety of synthetic modifications. Yet, the use of PFCP for fluorinated organic modified silica compounds is yet to be fully exploited.

Thus, there remains a need for fluorinated organic modified silica compounds and methods of synthesizing the same without evoking the environmental concerns associated with conventional methods.

SUMMARY OF THE INVENTION

The present invention overcomes the foregoing problems and other shortcomings, drawbacks, and challenges of synthesizing fluorinated organic modified silica compounds without evoking the environmental concerns. While the invention will be described in connection with certain embodiments, it will be understood that the invention is not limited to these embodiments. To the contrary, this invention includes all alternatives, modifications, and equivalents as may be included within the spirit and scope of the present invention.

In accordance with an embodiment of the present invention, a fluorinated cyclopentene functionalized silica material is provided that comprises a silica material having a fluorinated cyclopentene moiety covalently bonded thereto. Exemplary silica materials include a polysilsesquioxane, a nanosilica, a microsilica, a silica gel, a silica aerogel, or combinations thereof. The fluorinated cyclopentene moiety is based on a modification of perfluorocyclopentene (i.e., 1,2,3,3,4,4,5,5-octafluoro-1-cyclopentene) by nucleophilic substitution with an appropriate nucleophile. In accordance with another embodiment of the present invention, a method for preparing fluorinated cyclopentene functionalized silica materials is also provided.

In accordance with yet another embodiment of the present invention, a method of synthesizing fluorinated cyclopentene moieties is provided. The method is based on the exploitation of the reactive alkene functional group in PFCP using nucleophillic substitution, as well as hydrosilylation chemistries. Due to the unique reactivity of the unsaturated bond in PFCP, the fluorinated cyclopentene moieties can be synthesized such that they contain latent reactive groups, such as unsaturated bonds (e.g., alkene and/or alkyne) as well as a wide variety of different functional groups, providing a simple route for tailoring properties. Furthermore, the fluorinated cyclopentene moieties may be designed so as to contain alkoxysilane or chlorosilane reactive groups, which can be readily used in a sol-gel process for the preparation of fluorinated organic modified silicas. Accordingly, in a further aspect of the invention, new fluorinated cyclopentene moieties are also provided, which may be used to modify other materials.

In addition, the materials required in the syntheses are readily available and cost-effective, allowing for scalability. The use of the PFCP moiety in place of long perfluorinated carbon chains (e.g., $\geq C_6$) circumvents the environmental concerns associated with these fluorinated carbon chain compounds and at the same time retains the desired properties of the fluorinated organic modified silicas.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding.

DETAILED DESCRIPTION OF THE INVENTION

Figure 1:
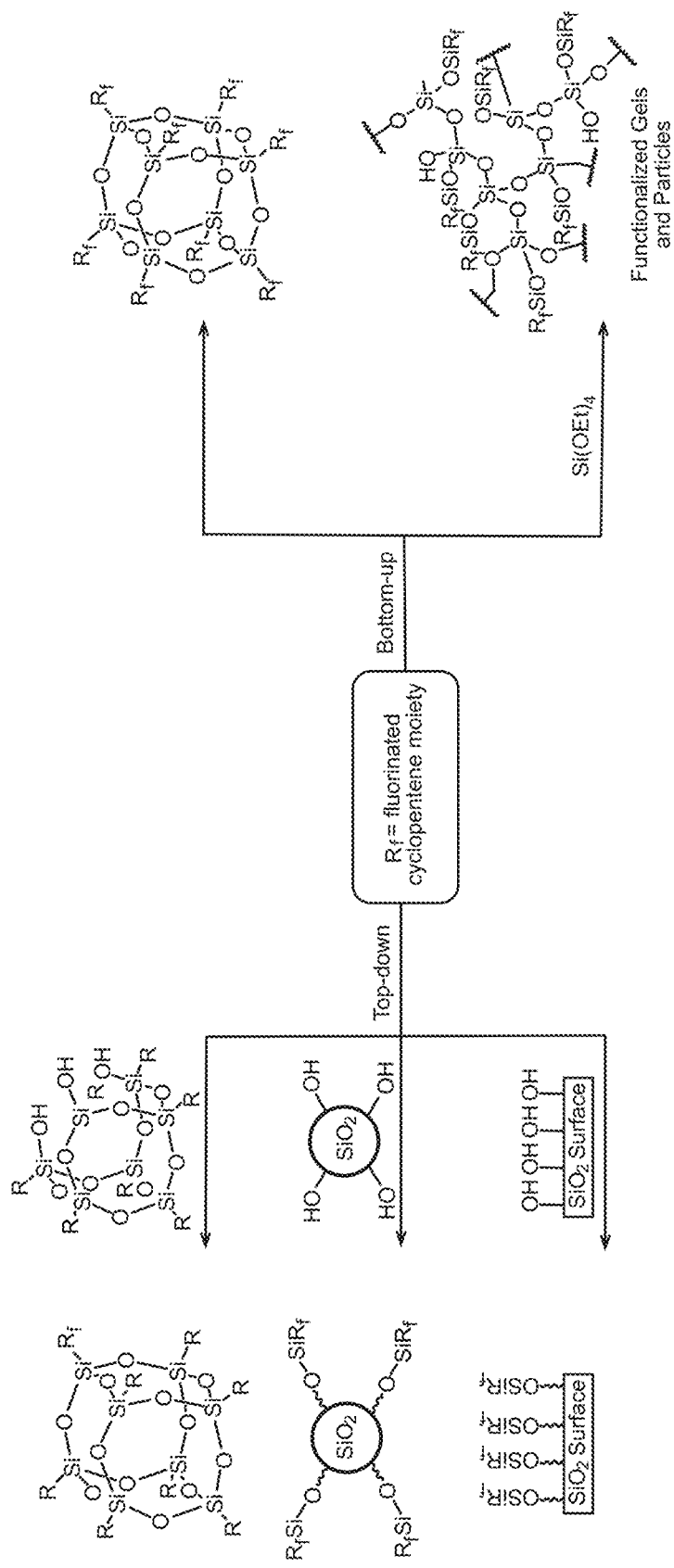
FIG. 1 is a schematic showing top-down and bottom-up approaches toward obtaining fluorinated organically modified silicates or silicas (F-ORMISILs), where $R_f$ represents a fluorinated organic component such as a fluorinated cyclopentene moiety, in accordance with embodiment s of the present invention.

In reference to FIG. 1, exemplary methods are provided for obtaining both network (e.g., particles, gels, or aerogels) and molecular (e.g., polysilsesquioxanes) fluorinated cyclopentene functionalized silica materials. In a top-down approach a fluorinated cyclopentene moiety ($R_f$) may be introduced into silica materials by employing fluorinated silanes (e.g., $(R_f)_nSiZ_{4-n}$, where Z may a labile group such as a halide (e.g., chloride), an alkoxy group (e.g., methoxy, ethoxy), or hydroxyl (OH)) to functionalize silanol terminated silsesquioxanes, particles, gels and other surfaces. In addition, network and molecular silicas can be prepared in a bottom-up fashion using sol-gel chemistry and fluorinated silanes. As a complement to this approach, a reactive functional group, via sol-gel chemistry, can be added to the silica framework, which is then followed by incorporating the fluorinated cyclopentene moiety ($R_f$) by post-modification of the functional group using other chemical transformations. In accordance with embodiments of the present invention, the fluorinated cyclopentene moiety is derived from perfluorocyclopentene (PFCP), which is also known as octafluorocyclopentene or 1,2,3,3,4,4,5,5-octafluoro-1-cyclopentene:

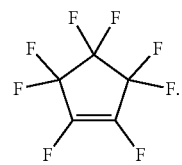

Figure 2:
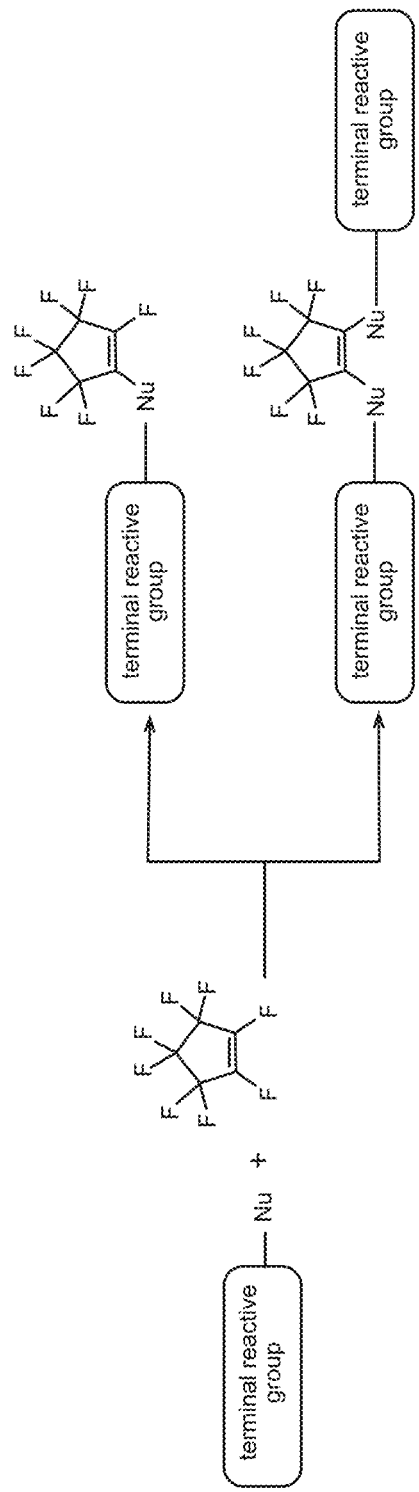
FIG. 2 is a schematic showing a general approach to preparing a fluorinated cyclopentene moiety, in accordance with an embodiment of the present invention.

Thus, in accordance with an embodiment of the present invention, a fluorinated cyclopentene functionalized silica material is provided that comprises a silica material having one or more fluorinated cyclopentene moieties covalently bonded thereto. Exemplary silica materials include a polysilsesquioxane, a nanosilica, a microsilica, a silica gel, a silica aerogel, or combinations thereof. The fluorinated cyclopentene moiety is based on a modification of perfluorocyclopentene (i.e., 1,2,3,3,4,4,5,5-octafluoro-1-cyclopentene) by nucleophilic substitution at one or both of the alkenyl fluorides with an appropriate nucleophile(s). In an embodiment, the nucleophile may be an appropriately functionalized silica material. In another embodiment, the nucleophile may include a reactive functional group, which enables further elaboration for coupling to the silica material. A general approach to preparing mono- and di-substituted fluorinated cyclopentene moieties is shown in FIG. 2.

In accordance with embodiments of the present invention, the fluorinated cyclopentene functionalized silica material comprises a fluorinated cyclopentene moiety that has a general chemical formula:

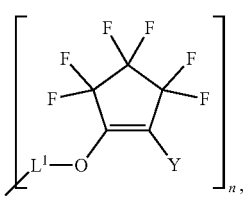

wherein L¹ is a linking group that covalently bonds the fluorinated cyclopentene moiety to the silica material; wherein Y is selected from the group consisting of F, OR¹, SR¹, and NR²R⁵, where R¹ is selected from the group consisting of substituted or unsubstituted alkyl, cycloalkyl, alkenyl, cycloalkenyl, alkynyl, aryl, heteroaryl, or heterocyclic; wherein R² and R⁵ are independently selected from the group consisting of H, substituted or unsubstituted alkyl, cycloalkyl, alkenyl, cycloalkenyl, alkynyl, aryl, heteroaryl, or heterocyclic; and wherein n is an integer equal to or greater than 1.

In another embodiment, Y can be OL², SL², or NR²L², wherein L² is a linking group that covalently bonds the fluorinated cyclopentene moiety to a second silica material. L¹ and L² can be carbon-containing chains or rings, such as substituted or unsubstituted alkyl, cycloalkyl, alkenyl, cycloalkenyl, alkynyl, aryl, heteroaryl, or heterocyclic groups.

In accordance with an embodiment of the present invention, the fluorinated cyclopentene moieties may be prepared using nucleophillic substitution and hydrosilylation chemistries. Because of the unique reactivity of the PFCP moiety, monomers may be synthesized so as to include latent reactive groups, as well as a wide variety of different functional groups, providing for a simple and straightforward route for tailoring properties. Exemplary latent reactive groups include unsaturated carbon-carbon bonds.

In accordance with an embodiment of the present invention, a method for the preparation of the fluorinated cyclopentene moiety is provided that begins with the nucleophilic substitution of PFCP using a substance having a sufficiently nucleophilic terminus, such as an OH, SH, or NH which can displace and substitute one (or both) of the alkenyl fluorides (see FIG. 2). Advantageously, the substance also includes a reactive group to allow additional chemistries (e.g., hydrosilylation reaction) to effect further elaboration. For example, PFCP may be reacted with a primary or secondary alcohol or thiol (or a primary or secondary amine) that further includes an alkene or alkyne reactive group. Preferably, the alkene or alkyne reactive group is a terminal alkene or alkyne group. In another example, PFCP or a mono-substituted PFCP may be reacted with 2-mercaptoethanol.

In one aspect PFCP may be reacted with a primary or secondary alcohol functional group (e.g., R¹OH), preferably in the presence of a base (e.g., tertiary amine bases such as triethylamine, N,N-diisopropylethylamine, or dimethylaminopyridine, or inorganic bases such as bicarbonate or carbonate) to scavenge the HF by-product. In one embodiment, R¹ may comprise a silica material itself to provide the fluorinated cyclopentene functionalized silica material directly. Alternatively, PFCP may be reacted with a primary or secondary alcohol (R¹OH) that further includes a reactive group, such as an alkene or an alkyne. Non-limiting examples of R¹ include, but are not limited to, propenyl, propynyl, butenyl, butynyl, or eugenyl (see FIG. 3).

Figure 3:
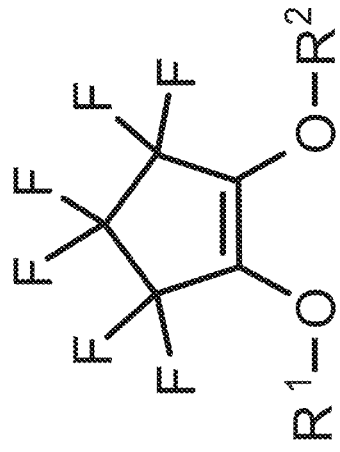
FIG. 3 is a schematic showing general formulas for two exemplary fluorinated cyclopentene moieties, in accordance with an embodiment of the present invention.
Figure 3:
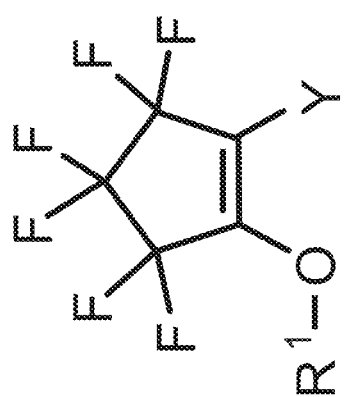

The fluorinated cyclopentene moieties (Formula 1 and Formula 2) shown in FIG. 3 are exemplary. The analogous sulfur (SR¹) and amino (NR²R⁵) variants are also envisioned. Each of R¹ and R² may be independently selected from the group consisting of substituted or unsubstituted alkyl, cycloalkyl, alkenyl, cycloalkenyl, alkynyl, aryl, heteroaryl, or heterocyclic groups, which also contain an alkene or alkyne reactive group. In an aspect of the invention, the alkene or alkyne reactive group may be a terminal group, which may be unsubstitued. According to an embodiment, R¹ and R² may be the same. Alternatively, in accordance with another embodiment, R¹ and R² may be different. Exemplary unsaturated alcohols include, but are not limited to, unsaturated C3 to C30 alcohols such as allyl alcohol (2-propen-1-ol), propargyl alcohol (2-propyn-1-ol), homoallyl alcohol (3-buten-1-ol), homopropargyl alcohol (3-butyn-1-ol), or eugenol (2-methoxy-4-(2-propenyl)phenol).

The displacement of the first alkenyl fluoride in PFCP by an alcohol/thiol/amine generally proceeds readily at or near room temperature (e.g., about 25° C.) using a slight stoichiometric excess of the desired nucleophile (alcohol, thiol, or amine). To achieve facile substitution of the second alkenyl fluoride with the same nucleophile, a stoichiometric excess should be used. Depending on the nucleophile, the displacement of the second alkenyl fluoride may be performed at an elevated temperature to induce the desired reaction and/or reduce reaction times. For example, it may be advantageous to heat the reaction mixture to about 50° C. when reacting a second alcohol nucleophile.

Figure 4:
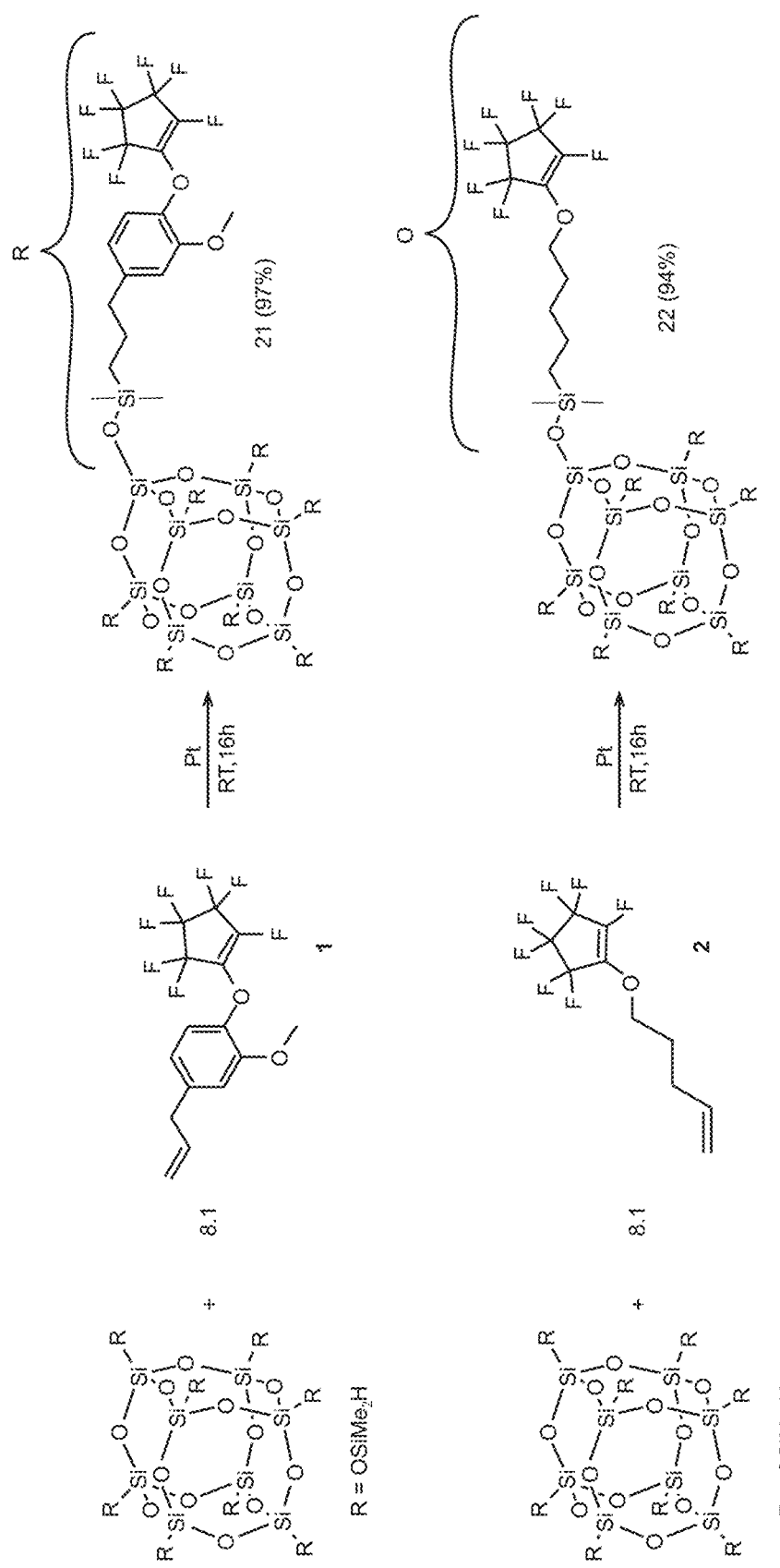
FIG. 4 is a schematic showing two exemplary fluorinated cyclopentene functionalized silsesquioxane compounds prepared via a top-down approach in FIG. 1 using a hydrosilylation reaction, in accordance with an embodiment of the present invention.

The fluorinated cyclopentene moieties (Formulas 1 and 2) shown in FIG. 3 may be used in a "top-down" approach (FIG. 1) by reaction with a selected organosilane, utilizing hydrosilylation chemistry with a platinum catalyst, to produce fluorinated organic modified silicas. Hydrosilylation, also called catalytic hydrosilation, describes the addition of Si—H bonds across unsaturated bonds in the presence of a catalyst, such as Speier's catalyst ($H_2PtCl_6$) or Karstedt's catalyst. Accordingly, the alkenyl or alkynyl functional group may be exploited to directly couple the fluorinated cyclopentene moiety to a silica material using the hydrosilylation reaction. As shown in FIG. 4, a reaction between a molecular silica, octakis(dimethylsiloxy)pentacyclo[9.5.1.1$^{3,9}$.1$^{5,15}$.1$^{7,13}$]octasiloxane (H-POSS), and 8.1 equivalents of Compound 1 or Compound 2, in the presence of a platinum catalyst, provides the functionalized molecular silicas, respectively.

Figure 5:
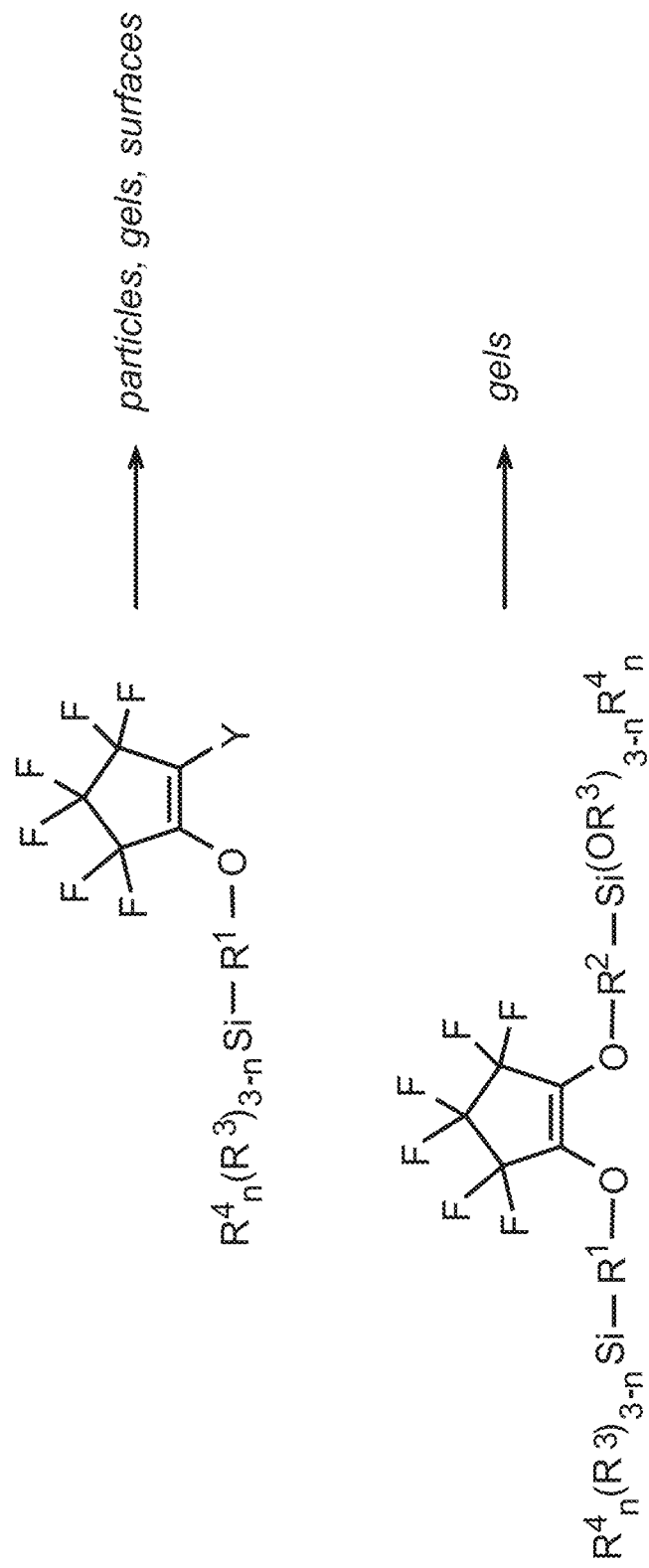
FIG. 5 is a schematic showing two general formulas for exemplary fluorinated cyclopentene moieties that may be used for making silica materials, such as nanosilicas, microsilicas, gels, aerogels, and/or surface modified silica materials, in accordance with an embodiment of the present invention.
Figure 6:
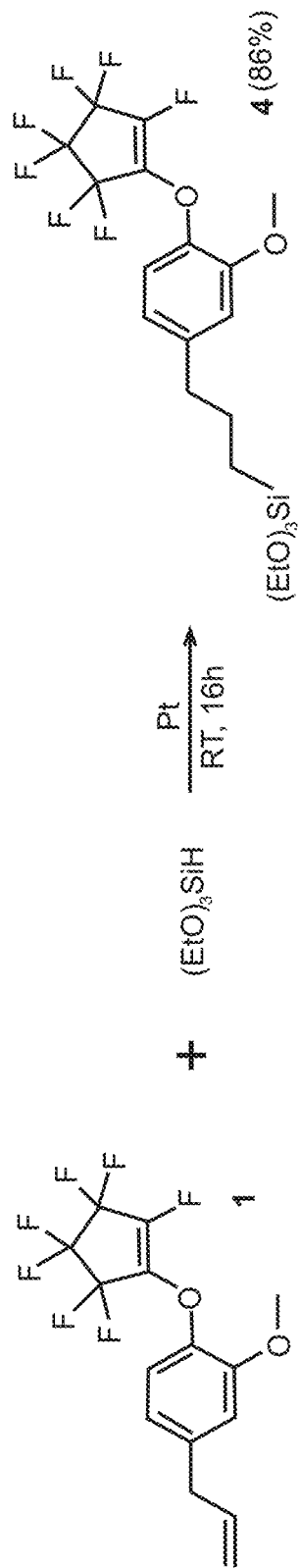
FIG. 6 is a schematic showing an exemplary approach to preparing a fluorinated cyclopentene moiety via a hydrosilylation reaction, in accordance with an embodiment of the present invention.
Figure 7:
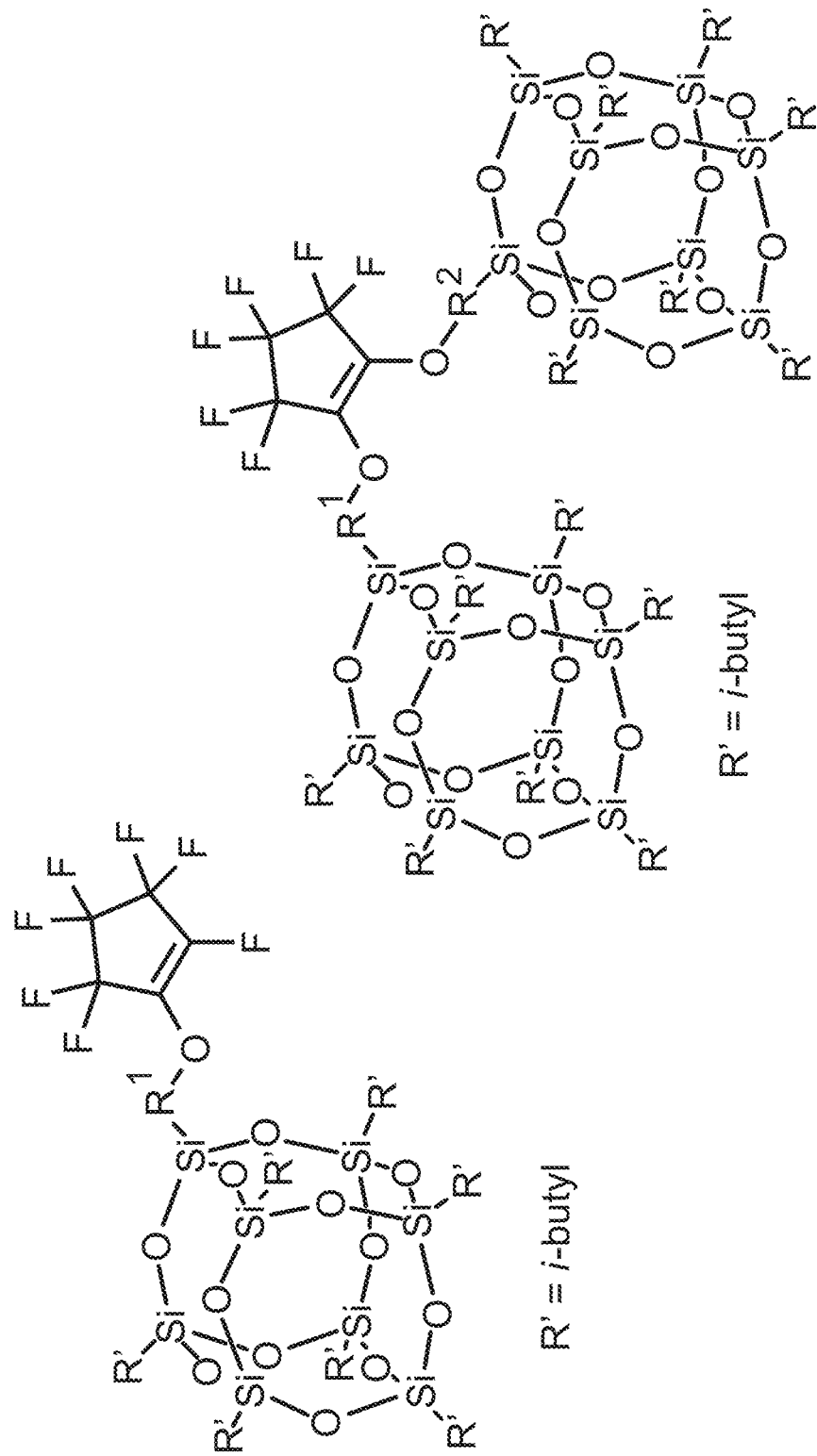
FIG. 7 is another schematic showing general formulas for two exemplary fluorinated cyclopentene functionalized silsesquioxane compounds prepared via the top-down approach shown in FIG. 1, in accordance with an embodiment of the present invention.

Alternatively, the alkenyl or alkynyl functional groups may be reacted with a mono-alkoxysilane ($R^4_2(R^3O)SiH$), a di-alkoxysilane, ($R^4(R^3O)_2SiH$), a tri-alkoxysilane (($R^3O)_3SiH$), or a chlorosilane (e.g., mono, di, or trichlorosilane), in the presence of an appropriate catalyst. $R^3$ and $R^4$ are typically C1 to C10 alkyl or cycloalkyl groups. The resultant hydrosilylation reaction product of the alkene or the alkyne, with the silane also provides a reactive functional group that may be exploited toward preparing the fluorinated cyclopentene functionalized silica material. An exemplary reaction between triethoxysilane and compound 1 is shown in FIG. 6. The resultant fluorinated cyclopentene moieties (such as the ones shown in FIGS. 5 and 6) may be used to modify a sol-gel (i.e., silica gel or aerogel). A "bottom-up" approach may be used for preparing fluorinated organic modified silicas, as well as, for functionalizing various silica surfaces. Additionally, the fluorinated cyclopentene moieties that contain three alkoxyls, hydroxyls, or chlorides may be used to corner-cap molecular silicas, such as endo-3,7,14-trihydroxy-1,3,5,7,9,11,14 heptaisobutyltricyclo[7.3.3.15, 11]heptasiloxane. According to another embodiment, the fluorinated cyclopentene moieties contain an alkoxysilane or chlorosilane reactive group, which can be readily used in the sol-gel process for the preparation of fluorinated organic modified silicas.

The implementation of the described PFCP-based modification of silica materials yields new materials that incorporate some degree of fluorination while alleviating the health and environmental concerns surrounding long perfluorinated carbon chains. Furthermore, the use of the hydrosilylation allows for the preservation of the PFCP ring in the resulting substances. This provided for a straightforward means to tailor properties through the post-modification of the latent reactive fluorine atom of the PFCP ring (in Formula [1] compounds) with other nucleophilic substances, such as hexafluoroisopropanol (HFIP) and 2-mercaptoethanol (2-ME). The ability to post-functionalize the PFCP ring and tune the properties was verified through multi-nuclear NMR and thermal analysis.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

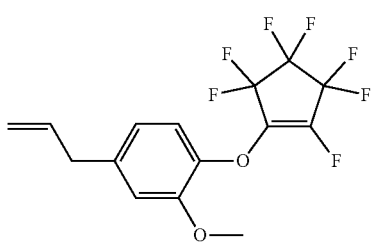 [SMILES: C=CCc1ccc(OC2=C(F)C(F)(F)C(F)(F)C2(F)F)c(OC)c1]

4-allyl-1-(2,3,3,4,4,5,5-heptafluorocyclopenten-1-yl)oxy-2-methoxy-benzene (Compound 1) was prepared using a 25 mL round bottom flask, equipped with a magnetic stir bar, and charged with dimethylformamide (($CH_3$)$_2$NCOH, "DMF") (12.0 mL), triethylamine (N($CH_2CH_3$)$_3$, 2.1 mL, 15.2 mmol), and eugenol ($CH_2CH_2CH_2C_6H_3$(O$CH_3$)OH, 2.3 mL, 15.0 mmol). The solution was stirred under $N_2$, and perfluorocyclopentene ($C_5F_8$, 1.0 mL, 7.5 mmol) was added using a syringe. The solution was stirred, under $N_2$, at room temperature, for 30 minutes. A GC-MS was taken to verify the conversion of reactants to products. The solution was then washed with brine, and the organics were extracted with ether. The ether layer was dried with $MgSO_4$, vacuum filtered, and all volatiles were removed under reduced pressure. The concentrated filtrate was added to a silica gel plug and then washed with hexane (250 mL/1.0 g of concentrated filtrate). Compound 1 was obtained as a clear and colorless liquid (2.3 g, 87.4%).

$^1$H NMR (CDCl$_3$, 300 MHz): δ 7.02 (d, aromatic, 1H, $^3J_{HH}$=8.1 Hz), 6.71-6.65 (m, aromatic, 2H), 5.93-5.79 (m, vinyl, 1H), 5.04-4.96 (m, vinyl, 2H), 3.74 (s, —OCH$_3$, 3H), 3.29 (d, CH$_2$=CHCH$_2$—, 2H, $^3J_{HH}$=6.9 Hz).

$^{13}$C NMR (CDCl$_3$, 100 MHz): δ 150.5 (aromatic C), 140.8 (aromatic C), 140.1 (aromatic C), 136.5 (CH$_2$=CHCH$_2$—), 120.6 (aromatic CH), 120.3 (aromatic CH), 116.2 (CH$_2$=CHCH$_2$—), 112.7 (aromatic CH), 55.3 (—OCH$_3$), 39.9 (CH$_2$=CHCH$_2$—).

$^{19}$F NMR(CDCl$_3$, 282 MHz): δ −115.4 (d, 2F, $^4J_{FF}$=13.5 Hz), −116.0 (d, 2F, $^3J_{FF}$=10.2 Hz), −129.8 (s, 2F), −157.0 to −157.2 (m, 1F).

Example 2

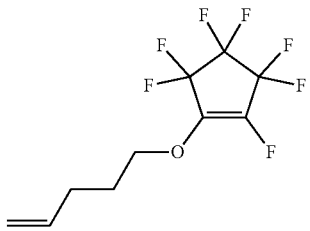 [SMILES: C=CCCCOC1=C(F)C(F)(F)C(F)(F)C1(F)F]

1,3,3,4,4,5,5-heptafluoro-2-pent-4-enoxy-cyclopentene (Compound 2) was prepared using the same method as in Example 2, using DMF (5.0 mL), triethylamine (0.30 mL, 2.2 mmol), 4-pentene-1-ol (CH$_2$CH$_2$CH$_2$CH$_2$CH$_3$OH, 0.20 mL, 1.9 mmol), and perfluorocyclopentene (0.50 mL, 3.7 mmol). The concentrated filtrate was added to a silica gel plug and then washed with ether (100 mL/0.30 g of concentrated filtrate). Compound 2 was obtained as a clear faint yellow liquid (0.48 g, 89.6%).

$^1$H NMR (CDCl$_3$, 400 MHz): δ 5.81-5.74 (m, vinyl, 1H), 5.08-5.02 (m, vinyl, 2H), 4.38 (t, d, —CH$_2$CH$_2$CH$_2$O—, 2H, $^3J_{HH}$=6.4 Hz, $^5J_{HF}$=2.8 Hz), 2.19 (q, CH$_2$=CHCH$_2$—, 2H, $^3J_{HH}$=7.2 Hz), 1.87 (p, —CH$_2$CH$_2$CH$_2$O—, 2H, $^3J_{HH}$=6.8 Hz).

$^{13}$C NMR (CDCl$_3$, 100 MHz): δ 136.4 (CH$_2$=CHCH$_2$—), 115.7 (CH$_2$=CHCH$_2$—), 72.6 (—CH$_2$CH$_2$CH$_2$O—), 29.1 (—CH$_2$CH$_2$CH$_2$O—), 28.1 (—CH$_2$CH$_2$CH$_2$O—).

$^{19}$F NMR(CDCl$_3$, 376 MHz): δ −114.8 (m, 2F), −116.2 to −116.3 (m, 2F), −129.6 (q, 2F, $^3J_{FF}$=), −162.3 to −162.4 (m, 1F).

Example 3

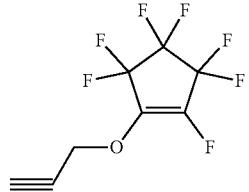 [SMILES: C#CCOC1=C(F)C(F)(F)C(F)(F)C1(F)F]

1,3,3,4,4,5,5-heptafluoro-2-prop-2-ynoxy-cyclopentene (Compound 3) was prepared using a 25 mL round bottom flask, equipped with a magnetic stir bar, was charged with DMF (2.0 mL) and Cs$_2$CO$_3$ (0.6 g, 1.9 mmol). The solution was cooled in an ice bath, under N$_2$, and perfluorocyclopentene (0.5 mL, 3.7 mmol) was added to the stirred solution. The propargyl alcohol (CHCCH$_2$OH, 0.1 mL, 1.9 mmol) was dissolved in DMF (10 mL) and added to an addition funnel. This solution was added slowly, drop-wise, over a 1.5 h period to the round bottom flask. The flask was kept in the ice bath during the addition. After the propargyl alcohol solution was added, the reaction flask was allowed to gradually warm to room temperature. A GC-MS was taken to verify the conversion of reactants to products. The solution was then washed with brine and the organics were extracted with ether. The ether layer was dried with MgSO$_4$, vacuum filtered, and all volatiles were removed under reduced pressure. Compound 3 was obtained as a clear, faint yellow liquid (0.76 g, 54.3%).

$^1$H NMR (CDCl$_3$, 400 MHz): δ 4.93 (bs, CHCCH$_2$O—, 2H), 2.71 (t, CHCCH$_2$O—, 1H, $^4J_{HH}$=2.6 Hz).

$^{13}$C NMR (CDCl$_3$, 75 MHz): δ 78.0 (CHCCH$_2$—), 74.4 (CHCCH$_2$—), 59.9 (CHCCH$_2$—).

$^{19}$F NMR(CDCl$_3$, 376 MHz): δ −115.2 (d, 2F, $^4J_{FF}$=13.9 Hz), 116.1 (d, 2F, $^3J_{FF}$=10.5 Hz), −129.5 to −129.6 (m, 2F), −158.8 to −159.0 (m, 1F).

Example 4

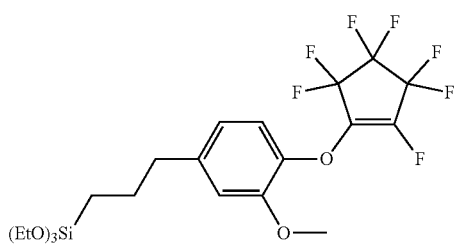

Triethoxy-[3-[4-(2,3,3,4,4,5,5-heptafluorocyclopenten-1-yl)oxy-3-methoxy-phenyl]propyl]silane (Compound 4) was prepared using a 25 mL round bottom flask, equipped with a magnetic stir bar, was charged with Compound 1 (1.0 g, 2.8 mmol), and 1 drop of Karstedt's catalyst (Pt-divinyltetramethyl-disiloxane complex in xylene). The solution was stirred under N$_2$, and then the triethoxysilane ((CH$_3$CH$_2$O)$_3$SiH, 0.5 mL, 2.8 mmol) was added, using a syringe. The solution was stirred, under N$_2$, at room temperature, overnight. A $^1$H NMR was taken to verify the conversion of reactants to products. All volatiles were removed under reduced pressure with low heat (range from about 35° C. to about 40° C.). Compound 4 was obtained as a clear and light yellow liquid (1.3 g, 85.7%).

$^1$H NMR (CDCl$_3$, 400 MHz): δ 7.06 (d, aromatic, 1H, $^3J_{HH}$=8.4 Hz), 6.77-6.72 (m, aromatic, 2H), 3.83 (s, —OCH$_3$, 3H), 3.81 (q, —OCH$_2$CH$_3$, 6H, $^3J_{HH}$=7.2 Hz), 2.63 (t, —SiCH$_2$CH$_2$CH$_2$—, 2H, $^3J_{HH}$=7.6 Hz), 1.73 (p, —SiCH$_2$CH$_2$CH$_2$—, 2H, $^3J_{HH}$=8.0 Hz), 1.20 (t, —OCH$_2$CH$_3$, 9H, $^3J_{HH}$=6.8 Hz), 0.65-0.61 (m, —SiCH$_2$CH$_2$CH$_2$—, 2H).

$^{13}$C NMR (CDCl$_3$, 100 MHz): δ 150.2 (aromatic C), 142.5 (aromatic C), 140.3 (aromatic C), 120.5 (aromatic CH), 120.1 (aromatic CH), 112.6 (aromatic CH), 58.1 (CH$_3$CH$_2$O—), 55.3 (—OCH$_3$), 38.7 (—SiCH$_2$CH$_2$CH$_2$—), 24.6 (—SiCH$_2$CH$_2$CH$_2$—), 17.9 (CH$_3$CH$_2$O—), 9.7 (—SiCH$_2$CH$_2$CH$_2$—).

$^{19}$F NMR(CDCl$_3$, 376 MHz): δ −115.3 (d, 2F, $^4J_{FF}$=13.5 Hz), −115.4 (d, 2F, $^3J_{FF}$=10.2 Hz), −129.7 (s, 2F), −157.0 to −157.2 (m, 1F).

Example 5

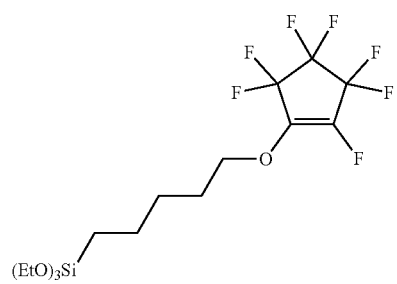

Triethoxy-[5-(2,3,3,4,4,5,5-heptafluorocyclopenten-1-yl)ocypentyl]silane (Compound 5) was prepared using the method of Example 4 with Compound 2 (0.72 g, 2.59 mmol), 1 drop of Karstedt's catalyst, and triethoxysilane (0.53 mL, 2.87 mmol). Compound 5 was obtained as a clear, light yellow liquid (1.04 g, 91.0%).

$^1$H NMR (CDCl$_3$, 400 MHz): δ 4.35 (t, d, —CH$_2$CH$_2$CH$_2$O—, 2H, $^3J_{HH}$=6.5 Hz, $^5J_{HF}$=2.8 Hz), 3.80 (q, (CH$_3$CH$_2$O)$_3$Si—, 6H, $^3J_{HH}$=7.1 Hz), 1.78-1.74 (m, —CH$_2$CH$_2$CH$_2$O—, 2H), 1.46-1.43 (m, —SiCH$_2$CH$_2$CH$_2$—, 4H), 1.21 (t, (CH$_3$CH$_2$O)$_3$Si—, 9H, $^3J_{HH}$=7.0 Hz), 0.63 (m, 2H, —SiCH$_2$CH$_2$CH$_2$—).

$^{13}$C NMR (CDCl$_3$, 100 MHz): δ 73.5 (—CH$_2$CH$_2$CH$_2$O—), 58.2 ((CH$_3$CH$_2$O)$_3$Si—), 28.7 (—CH$_2$CH$_2$CH$_2$O—), 28.4 (—CH$_2$CH$_2$CH$_2$O—), 22.3 (—SiCH$_2$CH$_2$CH$_2$—), 18.0 (CH$_3$CH$_2$O)$_3$Si), 10.1 (—SiCH$_2$CH$_2$CH$_2$—).

$^{19}$F NMR(CDCl$_3$, 376 MHz): δ −114.6 to −114.7 (m, 2F), −116.2 to −116.3 (m, 2F), −129.6 to −129.7 (m, 2F), −162.5 to −162.6 (m, 1F).

Example 6

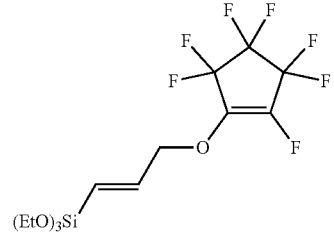

Triethoxy-[(E)-3-(2,3,3,4,4,5,5-heptafluorocyclopenten-1-yl)oxyprop-1-enyl]silane (Compound 6) was prepared using the method of Example 4 with Compound 3, 1 drop of Karstedt's catalyst was added, using a syringe.

Example 7

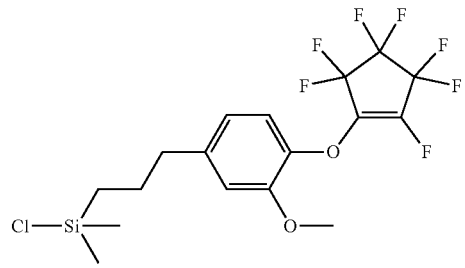 [SMILES: COc1cc(CCC[Si](C)(C)Cl)ccc1OC1=C(F)C(F)(F)C(F)(F)C1(F)F]

Chloro-[3-[4-(2,3,3,4,4,5,5-heptafluorocyclopenten-1-yl)oxy-3-methoxy-phenyl]propyl]-dimethylsilane (Compound 7) was prepared using the same method as Example 4, using low heat (50° C.) and Compound 1 (2.00 g, 5.64 mmol), chlorodimethylsilane (0.90 mL, 8.28 mmol), and 1 drop of Karstedt's catalyst. Compound 7 was obtained as a light brown, viscous liquid (2.43 g, 95.7%).

$^1$H NMR (CDCl$_3$, 400 MHz): δ 7.09 (d, aromatic, 1H, $^3J_{HH}$=8.4 Hz), 6.77-6.72 (m, aromatic, 2H), 3.84 (s, —OCH$_3$, 3H), 2.65 (t, —SiCH$_2$CH$_2$CH$_2$—, 2H, $^3J_{HH}$=7.6 Hz), 1.73 (p, —SiCH$_2$CH$_2$CH$_2$—, 2H, $^3J_{HH}$=8.1 Hz), 0.85-0.81 (m, —SiCH$_2$CH$_2$CH$_2$—, 2H), 0.40 (s, ClSi(CH$_3$)$_2$CH$_2$—, 6H).

$^{13}$C NMR (CDCl$_3$, 100 MHz): δ 150.4 (aromatic C), 142.2 (aromatic C), 140.5 (aromatic C), 120.5 (aromatic CH), 120.3 (aromatic CH), 112.7 (aromatic CH), 55.5 (—OCH$_3$), 38.8 (—SiCH$_2$CH$_2$CH$_2$—), 24.8 (—SiCH$_2$CH$_2$CH$_2$—), 18.4 (—SiCH$_2$CH$_2$CH$_2$—), 1.3 (ClSi(CH$_3$)$_2$CH$_2$—).

$^{19}$F NMR(CDCl$_3$, 376 MHz): δ −115.2 (d, 2F, $^3J_{FF}$=13.5 Hz), −115.9 (d, 2F, $^3J_{FF}$=10.9 Hz), −129.6 (s, 2F), −159.0 to −157.1 (m, 1F).

Example 8

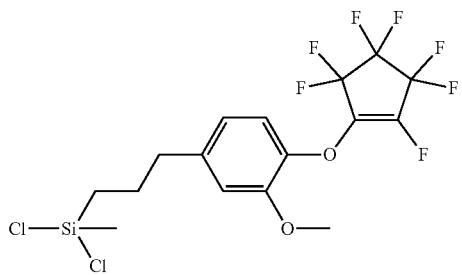 [SMILES: COc1cc(CCC[Si](C)(Cl)Cl)ccc1OC1=C(F)C(F)(F)C(F)(F)C1(F)F]

Dichloro-[3-[4-(2,3,3,4,4,5,5-heptafluorocyclopenten-1-yl)oxy-3-methoxy-phenyl]propyl]-methylsilane (Compound 8) was prepared using the same method as Example 4 using low heat (50° C.) and Compound 1 (0.50 g, 1.40 mmol), dichloromethylsilane (0.13 mL, 1.58 mmol), and 1 drop of Karstedt's catalyst. Compound 8 was obtained as a light yellow, viscous liquid (0.62 g, 93.5%).

$^1$H NMR (CDCl$_3$, 400 MHz): δ 7.10 (d, aromatic, 1H, $^3J_{HH}$=8.4 Hz), 6.77-6.72 (m, aromatic, 2H), 3.84 (s, —OCH$_3$, 3H), 2.68 (t, —SiCH$_2$CH$_2$CH$_2$—, 2H, $^3J_{HH}$=7.8 Hz), 1.85-1.81 (m, —SiCH$_2$CH$_2$CH$_2$—, 2H), 1.14-1.09 (m, —SiCH$_2$CH$_2$CH$_2$—, 2H), 0.76 (s, Cl$_2$Si(CH$_3$)CH$_2$—, 3H).

$^{13}$C NMR (CDCl$_3$, 100 MHz): δ 150.4 (aromatic C), 141.6 (aromatic C), 140.6 (aromatic C), 120.6 (aromatic CH), 120.4 (aromatic CH), 112.7 (aromatic CH), 55.5 (—OCH$_3$), 38.0 (—SiCH$_2$CH$_2$CH$_2$—), 24.1 (—SiCH$_2$CH$_2$CH$_2$—), 20.8 (—SiCH$_2$CH$_2$CH$_2$—), 4.7 (Cl$_2$Si(CH$_3$)CH$_2$—).

$^{19}$F NMR(CDCl$_3$, 376 MHz): δ −115.2 to −115.3 (m, 2F), −115.8 to −115.9 (m, 2F), −129.6 to −129.7 (m, 2F), −156.9 to −157.0 (m, 1F).

Example 9

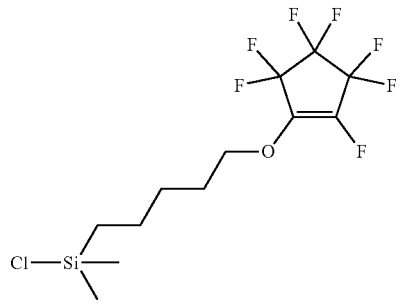 [SMILES: C[Si](C)(Cl)CCCCCOC1=C(F)C(F)(F)C(F)(F)C1(F)F]

Chloro-[5-(2,3,3,4,4,5,5-heptafluorocyclopenten-1-yl)oxypentyl]-dimethyl-silane (Compound 9) was prepared using the same method as Example 4, using low heat (50° C.) and Compound 2 (0.51 g, 1.83 mmol), chlorodimethylsilane (0.22 mL, 2.33 mmol), and 1 drop of Karstedt's catalyst. Compound 9 was obtained as a light brown liquid (0.68 g, 96.3%).

$^1$H NMR (CDCl$_3$, 400 MHz): δ δ 4.36 (t, d, —CH$_2$CH$_2$CH$_2$O—, 2H, $^3J_{HH}$=6.3 Hz, $^5J_{HF}$=2.9 Hz), 3.80 (p, —CH$_2$CH$_2$CH$_2$O—, 2H, $^3J_{HH}$=6.4 Hz), 1.50-1.46 (m, —CH$_2$CH$_2$CH$_2$O—, 4H), 0.85-0.81 (m, —SiCH$_2$CH$_2$CH$_2$—, 2H), 0.38 (s, ClSi(CH$_3$)$_2$CH$_2$—, 6H).

$^{13}$C NMR (CDCl$_3$, 100 MHz): δ 73.5 (—CH$_2$CH$_2$CH$_2$O—), 28.6 (—CH$_2$CH$_2$CH$_2$O—), 28.4 (—CH$_2$CH$_2$CH$_2$O—), 22.5 (—SiCH$_2$CH$_2$CH$_2$—), 18.6 (—SiCH$_2$CH$_2$CH$_2$—), 1.00 (ClSi(CH$_3$)$_2$CH$_2$—).

$^{19}$F NMR(CDCl$_3$, 376 MHz): δ −114.7 to −114.8 (m, 2F), −116.2 to −116.3 (m, 2F), −129.6 to −129.7 (m, 2F), −162.3 to −162.4 (m, 1F).

Example 10

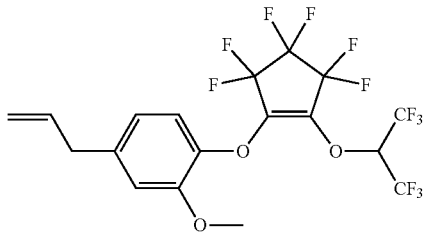 [SMILES: C=CCc1ccc(OC2=C(OC(C(F)(F)F)C(F)(F)F)C(F)(F)C(F)(F)C2(F)F)c(OC)c1]

4-allyl-1-[3,3,4,4,5,5-hexafluoro-2-[2,2,2-trifluoromethyl)ethoxy]cyclopenten-1-yl]oxy-2-methoxy-benzene (Compound 10) was prepared using a 25 mL r.b. flask, equipped with a stir bar, Compound 1 (0.38 g, 1.07 mmol), DMF (5 mL), 1,1,1,3,3,3-hexafluoro-2-propanol (0.15 mL, 1.14 mmol), and Cs$_2$CO$_3$ (0.22 g, 0.68 mmol). The solution was stirred at room temperature under N$_2$. A GC-MS was taken to verify the conversion of reactants to products. The solution was washed with brine and the organics were extracted with ether. The ether layer was dried with MgSO$_4$, vacuum filtered, and all volatiles were removed under reduced pressure. Compound 10 was obtained as a hazy orange liquid (0.41 g, 77.4%).

$^1$H NMR (CDCl$_3$, 400 MHz): δ 7.16 (d, aromatic, 1H, $^3J_{HH}$=8.8 Hz), 6.79-6.77 (m, aromatic, 2H), 5.97-5.88 (m, vinyl, 1H, —OCH(CF$_3$)$_2$, 1H), 5.12-5.03 (m, vinyl, 2H), 3.82 (s, —OCH$_3$, 3H), 3.38 (d, CH$_2$=CHCH$_2$C—, 2H, $^3J_{HH}$=6.8 Hz).

$^{13}$C NMR (CDCl$_3$, 100 MHz): δ 150.5 (aromatic C), 140.8 (aromatic C), 140.2 (aromatic C), 136.5 (CH$_2$=CHCH$_2$—), 121.5 (aromatic CH), 121.0 (aromatic CH), 116.3 (CH$_2$=CHCH$_2$—), 112.5 (aromatic CH), 73.8 (hep, —OCH(CF$_3$)$_2$, $^2J_{CF}$=34.5), 55.2 (—OCH$_3$), 39.9 (CH$_2$=CHCH$_2$—).

$^{19}$F NMR(CDCl$_3$, 376 MHz): δ −74.2 (d, 6F, J=5.3), −112.3 to −112.4 (m, 2F), −115.0 (bs, 2F), −129.9 (p, 2F, $^3J_{FF}$=3.3 Hz).

Example 11

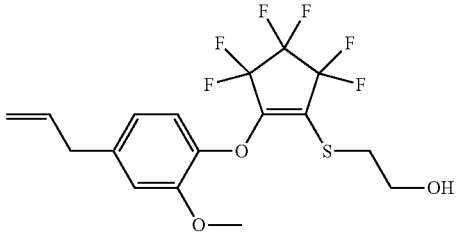 [SMILES: C=CCc1ccc(OC2=C(SCCO)C(F)(F)C(F)(F)C2(F)F)c(OC)c1]

2-[2-(4-allyl-2-methoxy-phenoxy)-3,3,4,4,5,5-hexafluoro-cyclopenten-1-yl]sulfanylethanol (Compound 11) was prepared using the same method as Example 10, using compound 1 (0.24 g, 0.67 mmol), DMF (1 mL), triethylamine (93 µL, 0.67 mmol), and 2-mercaptoethanol (47 µL, 0.67 mmol). Compound 11 was obtained as a hazy orange liquid (0.24 g, 85.7%).

$^1$H NMR (CDCl$_3$, 400 MHz): δ 7.06 (d, aromatic, 1H, $^3J_{HH}$=9.2 Hz), 6.77-6.74 (m, aromatic, 2H), 5.97-5.90 (m, vinyl, 1H), 5.11-5.05 (m, vinyl, 2H), 3.82 (s, —OCH$_3$, 3H), 3.67 (t, —SCH$_2$CH$_2$OH, 2H, $^3J_{HH}$=5.6 Hz), 3.51 (d, CH$_2$=CHCH$_2$C—, 2H, $^3J_{HH}$=6.4 Hz), 2.98 (t, —SCiCH$_2$OH, 2H, $^3J_{HH}$=5.8 Hz), 1.97 (bs, —CH$_2$CH$_2$OH, 1H).

$^{13}$C NMR (CDCl$_3$, 100 MHz): δ 150.6 (aromatic C), 140.8 (aromatic C), 139.8 (aromatic C), 136.7 (CH$_2$=CHCH$_2$—), 120.7 (aromatic CH), 120.6 (aromatic CH), 116.2 (CH$_2$=CHCH$_2$—), 112.7 (aromatic CH), 60.9 (—OCH$_2$CH$_2$S—), 55.2 (—OCH$_3$), 39.8 (CH$_2$=CHCH$_2$—), 35.1 (—OCH$_2$CH$_2$S—).

$^{19}$F NMR(CDCl$_3$, 376 MHz): δ −106.8 to −106.9 (m, 2F), −115.5 (hept, 2F, $^3J_{FF}$=2.6 Hz), −130.2 (p, 2F, $^3J_{FF}$=5.0 Hz).

Example 12

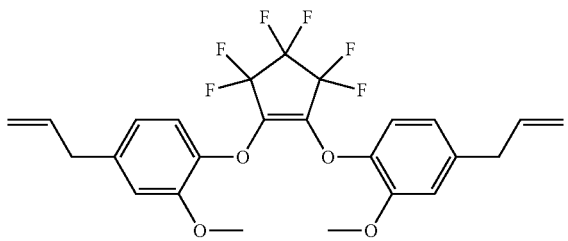 [SMILES: C=CCc1ccc(OC2=C(Oc3ccc(CC=C)cc3OC)C(F)(F)C(F)(F)C2(F)F)c(OC)c1]

4-allyl-1-[2-(4-allyl-2-methoxy-phenoxy)-3,3,4,4,5,5-hexafluoro-cyclopenten-1-yl]oxy-2-methoxy-benzene (Compound 12) was prepared in a 50 mL round bottom flask, equipped with a stir bar, and charged with DMF (6.0 mL), triethylamine (1.10 mL, 7.94 mmol), and eugenol (1.15 mL, 7.47 mmol). The solution was stirred under N$_2$, and then the perfluorocyclopentene (0.50 mL, 3.73 mmol) was added, using a syringe. The solution was stirred, under N$_2$, at room temperature, for 30 min. A GC-MS was taken to verify the conversion to the mono-substituted compound. Using the integration ratio from the GC-MS chromatogram, more eugenol and Cs$_2$CO$_3$ were added in a 2:1 mol ratio. The solution was gently heated (50° C.), under N$_2$, overnight. The conversion to the di-substituted compound was verified by GC-MS. The solution was then washed with brine and the organics were extracted with ether. The ether was then dried with MgSO$_4$, vacuum filtered, and all volatiles were removed under reduced pressure. The concentrated filtrate was added to a silica gel pad and then washed with a 3:1 DCM:hexane solution. All volatiles were removed under reduced pressure. Compound 12 was obtained as a clear and faint yellow, viscous liquid (1.75 g, 93.6%).

$^1$H NMR (CDCl$_3$, 300 MHz): δ 6.76 (d, aromatic, 2H, $^4J_{HH}$=8.4 Hz), 6.56-6.53 (m, aromatic, 4H), 5.95-5.86 (m, vinyl, 2H), 5.10-5.02 (m, vinyl, 4H), 3.73 (s, —OCH$_3$, 6H), 3.30 (d, CH$_2$=CHCH$_2$C—, 4H, $^3J_{HH}$=6.6 Hz).

$^{13}$C NMR (CDCl$_3$, 75 MHz): δ 149.4 (aromatic C), 141.8 (aromatic C), 137.8 (aromatic C), 137.0 (CH$_2$=CHCH$_2$—), 120.1 (aromatic CH), 118.2 (aromatic CH), 116.0 (CH$_2$=CHCH$_2$—), 112.5 (aromatic CH), 55.4 (—OCH$_3$), 39.8 (CH$_2$=CHCH$_2$—).

$^{19}$F NMR(CDCl$_3$, 282 MHz): δ −114.3 (t, 4F, $^3J_{FF}$=4.4 Hz), −130.3 (p, 2F, $^3J_{FF}$=4.2 Hz).

Example 13

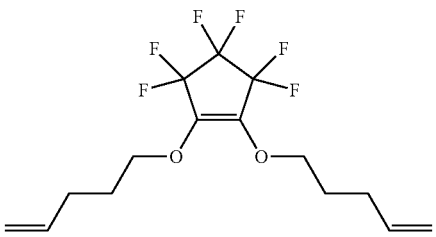 [SMILES: C=CCCCOC1=C(OCCCC=C)C(F)(F)C(F)(F)C1(F)F]

3,3,4,4,5,5-hexafluoro-1,2-bis(pent-4-enoxy)cyclopentene (Compound 13), was prepared using the same method as Example 12, using DMF (6 mL), 4-penten-1-ol (0.75 mL, 7.26 mmol), triethylamine (1.00 mL, 7.21 mmol), perfluorocyclopentene (0.50 mL, 3.73 mmol), and Cs$_2$CO$_3$ (1.20 g, 3.63 mmol). Compound 13 was purified using a silica gel plug and washed with ether (125 mL) and obtained as a clear golden/orange liquid (0.73 g, 56.9%).

$^1$H NMR (CDCl$_3$, 400 MHz): δ 5.79-5.75 (m, vinyl, 2H), 5.06-5.00 (m, H$_2$C=CHCH$_2$—, vinyl, 4H), 4.22 (t, —OCH$_2$CH$_2$CH$_2$—, 4H, $^3J_{HH}$=6.4 Hz), 2.16 (q, —OCH$_2$CH$_2$CH$_2$—, 4H, $^3J_{HH}$=7.2 Hz), 1.80 (p, —OCH$_2$CH$_2$CH$_2$—, 4H, $^3J_{HH}$=6.7 Hz).

$^{13}$C NMR (CDCl$_3$, 75 MHz): δ 136.0 (CH$_2$=CHCH$_2$—), 114.7 (CH$_2$=CHCH$_2$—), 70.8 (—CH$_2$CH$_2$CH$_2$O—), 28.5 (—CH$_2$CH$_2$CH$_2$O—), 27.7 (—CH$_2$CH$_2$CH$_2$O—).

$^9$F NMR(CDCl$_3$, 376 MHz): δ −111.7 (t, 4F, $^3J_{FF}$=5.5 Hz), −129.4 (p, 2F, $^3J_{FF}$=5.2 Hz).

Example 14

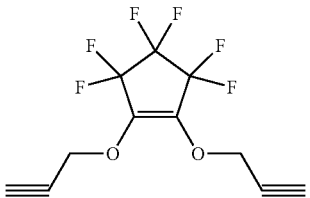 [SMILES: C#CCOC1=C(OCC#C)C(F)(F)C(F)(F)C1(F)F]

3,3,4,4,5,5-hexafluoro-1,2-bis(prop-2-ynoxy)cyclopentene (Compound 14) was prepared in a 25 mL round bottom flask and charged with a magnetic stir bar, DMF (5 mL), propargyl alcohol (0.20 mL, 3.42 mmol), and $Cs_2CO_3$ (0.56 g, 1.72 mmol). The solution was stirred under $N_2$ at room temperature. The perfluorocylcopentene (0.5 mL, 3.73 mmol) was added last. After 3 hours, a GC-MS was taken to determine the extent of the reaction. Aliquots of propargyl alcohol (0.10 mL, mmol) and $Cs_2CO_3$ (g, mmol) were added every 3 hours until the complete conversion to the desired product was observed by GC-MS analysis. The solution was then washed with brine and the organics were extracted with ether. The ether layer was dried with $MgSO_4$, vacuum filtered, and all volatiles were removed under reduced pressure. Compound 14 was obtained as a clear light golden-yellow liquid (0.64 g, 60.8%).

$^1$H NMR ($CDCl_3$, 400 MHz): δ 4.88 (d, $CHCCH_2O$—, 4H, $^4J_{HH}$=2.4 Hz), 2.66 (t, $CHCCH_2O$—, 2H, $^4J_{HH}$=2.2 Hz).
$^{13}$C NMR ($CDCl_3$, 100 MHz): δ 77.5 ($CHCCH_2$—), 76.0 ($CHCCH_2$—), 60.1 ($CHCCH_2$—).
$^{19}$F NMR($CDCl_3$, 376 MHz): δ −112.7 (t, 4F, $^3J_{FF}$=3.9 Hz), −129.8 (p, 2F, $^3J_{FF}$=4.4 Hz).

Example 15

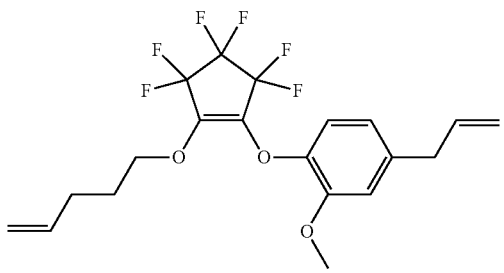 [SMILES: C=CCCCOC1=C(Oc2ccc(CC=C)cc2OC)C(F)(F)C(F)(F)C1(F)F]

4-allyl-1-(3,3,4,4,5,5-hexafluoro-2-pent-4-enoxy-cyclopenten-1-yl)oxy-2-methoxy-benzene (Compound 15) was prepared in a 25 mL round bottom flask, equipped with a stir bar, and charged with Compound 2 (0.33 g, 1.19 mmol) and DMF (1.5 mL). The solution was cooled in an ice bath under $N_2$. To the cold solution was added eugenol (0.20 mL, 1.3 mmol) and then $Cs_2CO_3$ (0.05 g, 0.15 mmol). The remaining $Cs_2CO_3$ was added in 0.05 g increments every hour until the reaction was complete, as determined by GC-MS. The solution was kept cold and stirred under $N_2$ for 1 hour. Once converted, the solution was then washed with brine and the organics were extracted with ether. The ether layer was dried with $MgSO_4$, vacuum filtered, and all volatiles were removed under reduced pressure. The concentrated filtrate was added to a silica gel pad and then washed with 120 mL of a 1:2 DCM:hexane solution. All volatiles were removed under reduced pressure and Compound 15 was obtained as a clear, faint yellow, liquid (0.38 g, 84.5%).

$^1$H NMR ($CDCl_3$, 400 MHz): δ 6.98 (d, aromatic, 1H, $^3J_{HH}$=7.6 Hz), 6.75-6.71 (m, aromatic, 2H), 5.98-5.88 (m, vinyl, 1H), 5.75-5.65 (m, 1H, vinyl), 5.10-5.05 (m, vinyl, 2H), 5.00-4.94 (m, 2H, vinyl), 4.22 (t, —$CH_2CH_2O$—, 2H, $^3J_{HH}$=6.4 Hz), 3.82 (s, —$OCH_3$, 3H), 3.35 (d, —$PhCH_2CH=CH_2$, 2H, $^3J_{HH}$=6.8 Hz), 2.00 (q, $CH_2=CHCH_2CH_2$—, 2H, $^3J_{HH}$=6.4 Hz), 1.64 (p, $CH_2=CHCH_2CH_2$—, 2H, $^3J_{HH}$=6.9 Hz).
$^{13}$C NMR ($CDCl_3$, 100 MHz): δ 115.0 (aromatic C), 142.0 (aromatic C), 137.9 (aromatic C), 136.4 (vinyl CH), 122.6 (vinyl CH), 120.2 (aromatic CH), 119.0 (aromatic CH), 115.6 (vinyl $CH_2$), 115.0 (vinyl $CH_2$), 112.4 (aromatic CH), 71.3 (—$CH_2CH_2CH_2O$—), 55.1 (—$OCH_3$) 39.5 (—$PhCH_2CH=CH_2$), 31.6 ($CH_2$), 28.1 ($CH_2$).
$^{19}$F NMR($CDCl_3$, 376 MHz): δ −113.1 (s, 2F), −115.0 (s, 2F), −130.8 (s, 2F).

Example 16

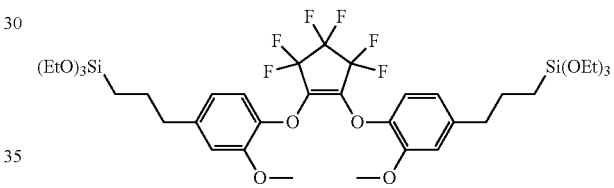

Triethoxy-[3-[4-[3,3,4,4,5,5-hexafluoro-2-[2-methoxy-4-(3-triethoxysilylpropyl)phenoxy]cyclopenten-1-yl]oxy-3-methoxy-phenyl]propyl]silane (Compound 16) was prepared using the same method as Example 4, using Compound 12 (0.22 g, 0.44 mmol), triethoxysilane (0.20 mL, 1.08 mmol) 1 drop of Karstedt's catalyst. Compound 16 was obtained as a clear light yellow, viscous liquid (0.34 g, 91.9%).

$^1$H NMR ($CDCl_3$, 400 MHz): δ 6.98 (d, aromatic C, 2H, $^3J_{HH}$=7.6 Hz), 6.54-6.53 (m, aromatic C, 4H), 3.80 (q, —$OCH_2CH_3$, 12 H, $^3J_{HH}$=6.2 Hz), 3.69 (s, 6H, —$OCH_3$), 2.52 (t, —$SiCH_2CH_2CH_2$—, 4H, $^3J_{HH}$=7.6 Hz), 1.65 (p, —$SiCH_2CH_2CH_2$—, 4H, $^3J_{HH}$=7.9 Hz), 1.20 (t, —$OCH_2CH_3$, 18H, $^3J_{HH}$=6.8 Hz), 0.63-0.59 (m, —$SiCH_2CH_2CH_2$—, 4H).
$^{13}$C NMR ($CDCl_3$, 75 MHz): δ 149.3 (aromatic C), 141.5 (aromatic C), 140.1 (aromatic C), 120.0 (aromatic CH), 118.1 (aromatic CH), 112.5 (aromatic CH), 58.3 (—$OCH_2CH_3$), 55.5 (—$OCH_3$), 38.9 (—$SiCH_2CH_2CH_2$—), 24.9 (—$SiCH_2CH_2CH_2$—), 18.2 (—$OCH_2CH_3$), 10.0 (—$SiCH_2CH_2CH_2$—).
$^{19}$F NMR($CDCl_3$, 376 MHz): δ −114.3 (t, 4F), −130.3 to −130.4 (m, 2F).

Example 17

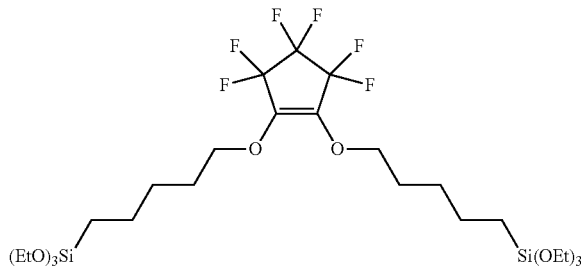

Triethoxy-[5-[3,3,4,4,5,5-hexafluoro-2-(5-triethoxysilyl-pentoxy)cyclopenten-1-yl]oxypentyl]silane (Compound 17) was prepared using the same method as Example 4, using Compound 13 (0.43 g, 1.25 mmol)), triethoxysilane (0.50 mL, 2.71 mmol), and 1 drop of Karstedt's catalyst. Compound 17 was obtained as a light brown, viscous liquid (0.76 g, 90.5%).

$^1$H NMR (CDCl$_3$, 400 MHz): δ 4.18 (t, —OCH$_2$CH$_2$CH$_2$—, 4H, $^3J_{HH}$=6.6 Hz), 3.80 (q, —Si(OCH$_2$CH$_3$)$_3$, 12H, $^3J_{HH}$=7.1 Hz), 1.70-1.67 (m, —OCH$_2$CH$_2$CH$_2$—, 4H), 1.43-1.41 (m, —OCH$_2$CH$_2$CH$_2$—, 4H, —CH$_2$CH$_2$Si—, 4H), 1.21 (t, —Si(OCH$_2$CH$_3$)$_3$, 18H, $^3J_{HH}$=7.0 Hz), 0.64-0.60 (m, —CH$_2$CH$_2$Si—, 4H).

$^{13}$C NMR (CDCl$_3$, 75 MHz): δ 72.5 (—OCH$_2$CH$_2$CH$_2$—), 58.3 (—Si(OCH$_2$CH$_3$)$_3$), 29.2 (—OCH$_2$CH$_2$CH$_2$—), 28.8 (—OCH$_2$CH$_2$CH$_2$—), 22.5 (—CH$_2$CH$_2$Si—), 18.2 (—Si(OCH$_2$CH$_3$)$_3$), 10.32 (—CH$_2$CH$_2$Si—).

$^{19}$F NMR(CDCl$_3$, 376 MHz): δ −111.6 (t, 4F, $^3J_{FF}$=5.5 Hz), −129.3 to −129.4 (2F).

Example 18

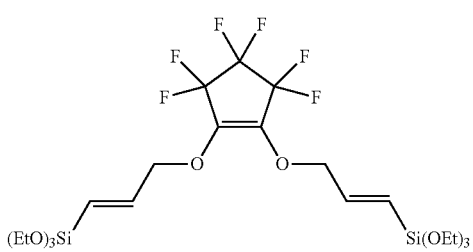

Triethoxy-[(E)-3-[3,3,4,4,5,5-hexafluoro-2-[(E)-3-triethoxysilylallyl-oxy]cyclopenten-1-yl]oxyprop-1-enyl]silane (Compound 18) was prepared using the same method as Example 4, using Compound 14, triethoxysilane, 1 drop of Karstedt's catalyst.

Example 19

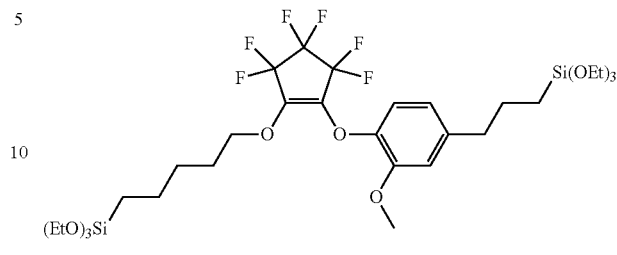

Triethoxy-[5-[3,3,4,4,5,5-hexafluoro-2-[2-methoxy-4-(3-triethoxysilyl-propyl)phenoxy]cyclopenten-1-yl]oxypentyl]silane (Compound 19) was prepared using the same method as Example 4, using Compound 15 (0.91 g, 2.15 mmol), triethoxysilane (1.00 mL, 5.42 mmol), and 1 drop of Karstedt's catalyst. Compound 19 was obtained as a light yellow liquid (1.54 g, 95.1%).

$^1$H NMR (CDCl$_3$, 400 MHz): δ 6.94 (d, aromatic, 1H, $^3J_{HH}$=8.0 Hz), 6.73-6.68 (m, aromatic, 2H), 4.24 (t, —OCH$_2$CH$_2$CH$_2$—, 2H, $^3J_{HH}$=6.4 Hz), 3.84-3.73 (m, —OCH$_3$, —Si(OCH$_2$CH$_3$)$_3$, 15H), 2.59 (t, —CH$_2$CH$_2$CH$_2$Si—, 2H, $^3J_{HH}$=7.8 Hz), 1.72-1.65 (m, —OCH$_2$CH$_2$CH$_2$—, 2H), 1.59-1.55 (m, —OCH$_2$CH$_2$CH$_2$—, 2H), 1.35-1.30 (m, —CH$_2$CH$_2$CH$_2$Si—, 4H), 1.19 (t, d —Si(OCH$_2$CH$_3$)$_3$, 18H, $^3J_{HH}$=7 Hz, $^3J_{HH}$=1.6 Hz), 0.65-0.56 (m, —CH$_2$CH$_2$Si—, 4H).

$^{13}$C NMR (CDCl$_3$, 75 MHz): δ 150.1 (aromatic C), 142.0 (aromatic C), 140.6 (aromatic C), 120.4 (aromatic CH), 119.0 (aromatic CH), 112.8 (aromatic CH), 72.6 (—OCH$_2$CH$_2$CH$_2$), 58.2 (—Si(OCH$_2$CH$_3$)$_3$), 58.1 (—Si(OCH$_2$CH$_3$)$_3$), 55.5 (—OCH$_3$), 38.7 (—SiCH$_2$CH$_2$CH$_2$—), 28.9 (—SiCH$_2$CH$_2$CH$_2$—), 28.5 (—SiCH$_2$CH$_2$CH$_2$—), 24.7 (—SiCH$_2$CH$_2$CH$_2$—), 22.3 (—SiCH$_2$CH$_2$CH$_2$—), 18.1 (—Si(OCH$_2$CH$_3$)$_3$), 10.2 (—SiCH$_2$CH$_2$CH$_2$—), 9.9 (—SiCH$_2$CH$_2$CH$_2$—).

$^{19}$F NMR(CDCl$_3$, 376 MHz): δ −112.0 to −112.1 (m, 2F), −114.8 to −114.9 (m, 2F), −130.1 (p, 2F, $^3J_{FF}$=4.5 Hz).

Example 20

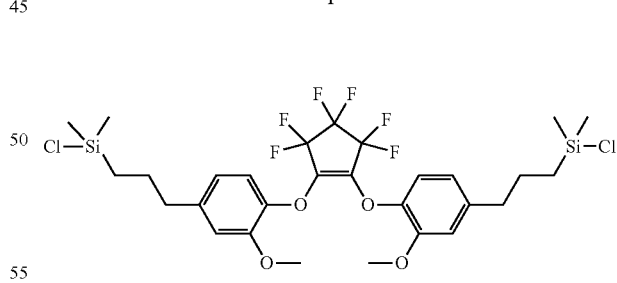

Chloro-[3 [4-[2-[4-[3-[chloro(dimethyl)silyl]propyl]-2-methoxy-phenoxy]-3,3,4,4,5,5-hexafluoro-cyclopenten-1-yl]oxy-3-methoxy-phenyl]propyl]-dimethyl-silane (Compound 20) was prepared using the same method as Example 4, using low heat (50° C.) and Compound 12 (0.55 g, 1.10 mmol), chlorodimethylsilane (0.25 mL, 2.30 mmol), and 1 drop of Karstedt's catalyst. Compound 20 was obtained as a light brown liquid (0.61 g, 93.8%).

$^1$H NMR (CDCl$_3$, 400 MHz): δ 6.70 (d, aromatic, 2H, $^3J_{HH}$=8.0 Hz), 6.53-6.50 (m, aromatic, 4H), 3.71 (s, —OCH$_3$, 6H), 2.54 (t, —SiCH$_2$CH$_2$CH$_2$—, 4H, $^3J_{HH}$=7.6

Hz), 1.69-1.61 (m, —SiCH$_2$CH$_2$CH$_2$—, 4H), 0.82-0.78 (m, —SiCH$_2$CH$_2$CH$_2$—, 4H), 0.38 (s, ClSi(CH$_3$)$_2$CH$_2$—, 6H).

$^{13}$C NMR (CDCl$_3$, 100 MHz): δ 149.4 (aromatic C), 141.6 (aromatic C), 139.8 (aromatic C), 120.0 (aromatic CH), 118.0 (aromatic CH), 112.5 (aromatic CH), 55.5 (—OCH$_3$), 38.7 (—SiCH$_2$CH$_2$CH$_2$—), 25.1 (—SiCH$_2$CH$_2$CH$_2$—), 18.5 (—SiCH$_2$CH$_2$CH$_2$—), 1.5 (ClSi(CH$_3$)$_2$CH$_2$—).

$^{19}$F NMR(CDCl$_3$, 376 MHz): δ −114.2 (t, 4F, $^3J_{FF}$=4.7 Hz), −130.3 (p, 2F, $^3J_{FF}$=4.4 Hz).

Example 21

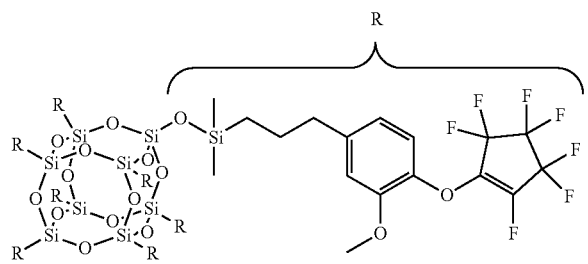

A molecular silica (Compound 21) was prepared in a 15 mL round bottom flask, equipped with a stir bar, and charged with Compound 1 (0.23 g, 0.65 mmol) and 1 drop of Karsteadt's catalyst. It was stirred at room temperature under N$_2$. OctaSilane POSS (0.07 g, 0.069 mmol) was added last. The solution was stirred at room temperature, under N$_2$, overnight. Compound 21 was obtained as a clear, golden yellow, viscous liquid (0.29 g, 96.7%).

$^1$H NMR (CDCl$_3$, 400 MHz): δ 7.04 (d, aromatic, 8H, $^3J_{HH}$=8.0 Hz), 6.70-6.65 (m, aromatic, 16H), 3.79 (s, —OCH$_3$, 24H), 2.54 (t, —Si(CH$_3$)$_2$CH$_2$CH$_2$CH$_2$—, 16H, $^3J_{HH}$=7.6 Hz), 1.63-1.59 (m, —Si(CH$_3$)$_2$CH$_2$CH$_2$CH$_2$—, 16H), 0.60-0.55 (m, —Si(CH$_3$)$_2$CH$_2$CH$_2$CH$_2$—, 16H), 0.07 (s, —Si(CH$_3$)$_2$CH$_2$CH$_2$CH$_2$—, 48H).

$^{13}$C NMR (CDCl$_3$, 100 MHz): δ 150.2 (aromatic C), 142.3 (aromatic C), 140.4 (aromatic C), 120.4 (aromatic CH), 120.3 (aromatic CH), 112.7 (aromatic CH), 55.7 (—OCH$_3$), 39.2 (—SiCH$_2$CH$_2$CH$_2$—), 24.7 (—SiCH$_2$CH$_2$CH$_2$—), 17.2 (—SiCH$_2$CH$_2$CH$_2$—), −0.5 (—Si(CH$_3$)$_2$CH$_2$—).

$^{19}$F NMR(CDCl$_3$, 376 MHz): δ −115.3 (d, 2F, $^3J_{FF}$=12.0 Hz), −116.0 (d, 2F, $^3J_{FF}$=10.9 Hz), −129.7 (s, 16F), −157.2 to −157.3 (m, 8F).

Example 22

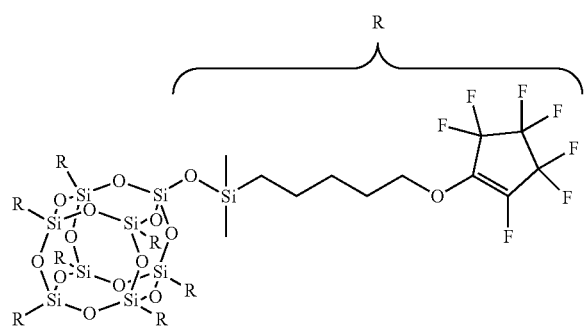

A molecular silica, Compound 22, was synthesized using the same procedure as in Example 21, using compound 2 (0.15 g, 0.54 mmol), 1 drop of Karsteadt's catalyst, and Octasilane POSS (0.06 g, 0.059 mmol). Compound 22 was obtained as a clear, golden yellow, viscous liquid (0.19 g, 94.2%).

$^1$H NMR (CDCl$_3$, 400 MHz): δ 4.34 (t, d, —OCH$_2$CH$_2$CH$_2$—, 16H, $^3J_{HH}$=6.3 Hz, $^5J_{HF}$=2.9 Hz), 1.74 (p, —OCH$_2$CH$_2$CH$_2$—, 16H, $^3J_{HH}$=6.8 Hz), 1.45-1.34 (m, —CH$_2$CH$_2$CH$_2$Si—, 32H), 0.61-0.57 (m, —CH$_2$CH$_2$CH$_2$Si— 16H), 0.11 (s, —Si(CH$_3$)$_2$CH$_2$—, 48H).

$^{13}$C NMR (CDCl$_3$, 75 MHz): δ 74.2 (—CH$_2$CH$_2$CH$_2$O—), 29.4 (—CH$_2$CH$_2$CH$_2$O—), 23.1 (—SiCH$_2$CH$_2$CH$_2$—), 18.0 (—SiCH$_2$CH$_2$CH$_2$—), 1.5 (—SiCH$_2$CH$_2$CH$_2$—), −0.1 (—Si(CH$_3$)$_2$CH$_2$—).

$^{19}$F NMR(CDCl$_3$, 376 MHz): δ −114.7 to −114.8 (m, 16F), −116.3 to −116.4 (m, 16F), −129.6 to −129.7 (m, 16F), −162.6 (bs, 8F).

Example 23

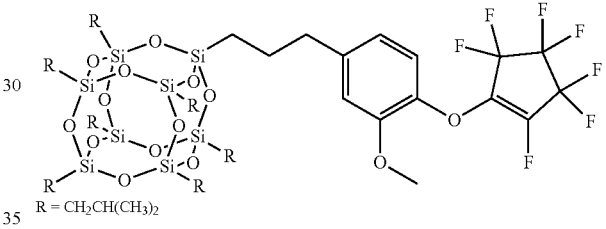

R = CH$_2$CH(CH$_3$)$_2$

A molecular silica, Compound 23, was prepared using 15 mL r.b. flask, equipped with a stir bar, Compound 1 (1.17 g, 3.28 mmol) and 1 drop of Karsteadt's catalyst. Hydride substituted poly(isobutylsilsesquioxane) (2.00 g, 2.45 mmol) was dissolved in toluene (1.50 mL) and added to the flask with stirring. The solution was gently heated (75-80° C.), under N$_2$, for two days. All volatiles were removed under reduced pressure and the resulting material was re-suspended in MeOH. Compound 23 was obtained as an off white powder (1.80 g, 63%).

$^1$H NMR (CDCl$_3$, 400 MHz): δ 7.07 (d, aromatic, 1H, $^3J_{HH}$=8.0 Hz), 6.73-6.72 (m, aromatic, 2H), 3.82 (s, —OCH$_3$, 3H), 2.61 (t, —SiCH$_2$CH$_2$CH$_2$—, 2H, $^3J_{HH}$=7.4 Hz), 1.88-1.79 (m, —CH$_2$CH(CH$_3$)$_2$, 7H), 1.72-1.68 (m, —SiCH$_2$CH$_2$CH$_2$—, 2H), 0.95-0.92 (m, —CH$_2$CH(CH$_3$)$_2$, 42H), 0.63-0.57 (m, —CH$_2$CH(CH$_3$)$_2$, 14H, —SiCH$_2$CH$_2$CH$_2$—, 2H).

$^{13}$C NMR (CDCl$_3$, 100 MHz): δ 150.2 (aromatic C), 142.5 (aromatic C), 140.4 (aromatic C), 120.5 (aromatic CH), 120.2 (aromatic CH), 112.7 (aromatic CH), 55.7 (—OCH$_3$), 38.7 (—SiCH$_2$CH$_2$CH$_2$—), 25.6 (—CH$_2$CH(CH$_3$)$_2$), 24.7 (—SiCH$_2$CH$_2$CH$_2$—), 23.8 ((—CH$_2$CH(CH$_3$)$_2$), 22.5 (—CH$_2$CH(CH$_3$)$_2$), 11.7 (—SiCH$_2$CH$_2$CH$_2$—).

$^{19}$F NMR(CDCl$_3$, 376 MHz): δ −115.3 (d, 2F, $^3J_{FF}$=12.0 Hz), −116.0 (d, 2F, $^3J_{FF}$=10.9 Hz), −129.7 (s, 2F), −157.2 to −157.3 (m, 1F).

Example 24

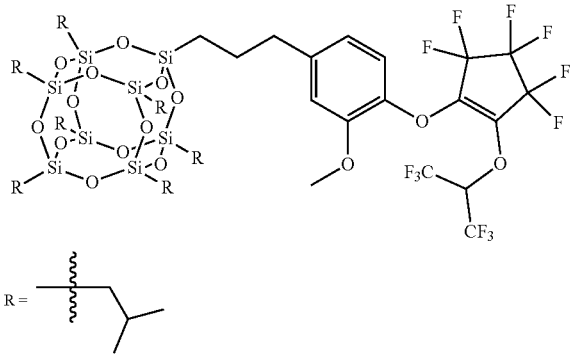

A molecular silica (Compound 24) was prepared using the same method as Example 10, using Compound 23 (0.42 g, 0.36 mmol), THF (2 mL), DMF (3 mL), Cs$_2$CO$_3$ (0.08 g, 0.24 mmol), and hexafluoro-2-propanol (50 μL, 0.38 mmol). Compound 24 was obtained as a fine off white powder (0.42 g, 88%).

$^1$H NMR (CDCl$_3$, 400 MHz): δ 7.13 (d, aromatic, 1H, $^3J_{HH}$=8.4 Hz), 6.74-6.72 (m, aromatic, 2H), 5.89 (h, —OCH (CF$_3$)$_2$, 1H, $^3J_{HF}$=5.6 Hz), 3.80 (s, —OCH$_3$, 3H), 2.61 (t, —SiCH$_2$CH$_2$CH$_2$—, 2H, $^3J_{HH}$=7.6 Hz), 1.87-1.79 (m, —CH$_2$CH(CH$_3$)$_2$, 7H), 1.72-1.68 (m, —SiCH$_2$CH$_2$CH$_2$—, 2H), 0.95-0.92 (m, —CH$_2$CH(CH$_3$)$_2$, 42H), 0.63-0.57 (m, —CH$_2$CH(CH$_3$)$_2$, 14H, —SiCH$_2$CH$_2$CH$_2$—, 2H).

$^{13}$C NMR (CDCl$_3$, 100 MHz): δ 150.5 (aromatic C), 142.8 (aromatic C), 139.9 (aromatic C), 121.4 (aromatic CH), 120.8 (aromatic CH), 112.4 (aromatic CH), 73.9 (h, —OCH(CF$_3$)$_2$, $^2J_{CF}$=33.5 Hz), 55.7 (—OCH$_3$), 38.7 (—SiCH$_2$CH$_2$CH$_2$—), 25.6 (—CH$_2$CH(CH$_3$)$_2$), 24.7 (—SiCH$_2$CH$_2$CH$_2$—), 23.8 ((—CH$_2$CH(CH$_3$)$_2$), 22.5 (—CH$_2$CH(CH$_3$)$_2$), 11.7 (—SiCH$_2$CH$_2$CH$_2$—).

$^{19}$F NMR(CDCl$_3$, 376 MHz): δ −74.1 (d, 6F, $^3J_{HF}$=5.6 Hz), −112.3 (s, 2F), −114.8 (s, 2F), −129.7 to −129.8 (m, 2F).

Example 25

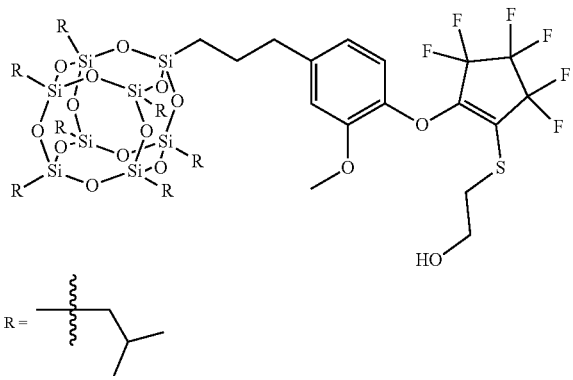

A molecular silica (Compound 25) was prepared using the same method as Example 10, using compound 23 (0.67 g, 0.57 mmol), THF (2 mL), and DMF (5 mL), triethylamine (81 μL, 0.58 mmol), and 2-mercaptoethanol (43 μL, 0.61 mmol). Compound 25 was obtained as an off white/faint yellow waxy solid (0.67 g, 94.4%).

$^1$H NMR (CDCl$_3$, 400 MHz): δ 7.04 (d, aromatic, 1H, $^3J_{HH}$=8.4 Hz), 6.73-6.71 (m, aromatic, 2H), 3.81 (s, —OCH$_3$, 3H), 3.67 (q, —SCH$_2$CH$_2$OH, 2H, $^3J_{HH}$=6.7 Hz), 2.99 (t, —SCH$_2$CH$_2$OH, 2H, $^3J_{HH}$=5.8 Hz), 2.61 (t, —SiCH$_2$CH$_2$CH$_2$—, 2H, $^3J_{HH}$=7.6 Hz), 1.88-1.78 (m, —CH$_2$CH(CH$_3$)$_2$, 7H), 1.73-1.69 (m, —SiCH$_2$CH$_2$CH$_2$—, 2H), 0.95-0.92 (m, —CH$_2$CH(CH$_3$)$_2$, 42H), 0.63-0.57 (m, —CH$_2$CH(CH$_3$)$_2$, 14H, —SiCH$_2$CH$_2$CH$_2$—, 2H).

$^{13}$C NMR (CDCl$_3$, 100 MHz): δ 150.5 (aromatic C), 142.3 (aromatic C), 140.2 (aromatic C), 120.7 (aromatic CH), 120.6 (aromatic CH), 112.6 (aromatic CH), 60.8 (—SCH$_2$CH$_2$OH), 55.8 (—OCH$_3$), 38.6 (—SiCH$_2$CH$_2$CH$_2$—), 35.7 (—SCH$_2$CH$_2$OH), 25.7 (—CH$_2$CH(CH$_3$)$_2$), 24.7 (—SiCH$_2$CH$_2$CH$_2$—), 23.9 ((—CH$_2$CH(CH$_3$)$_2$), 22.5 (—CH$_2$CH(CH$_3$)$_2$), 11.7 (—SiCH$_2$CH$_2$CH$_2$—).

$^{19}$F NMR(CDCl$_3$, 376 MHz): δ −106.9 (bs, 2F), −115.5 (p, 2F, J$_{FF}$=2.6 Hz), −130.2 (p, 2F, J$_{FF}$=4.8 Hz).

Example 26

Silica nanoparticles were prepared following the Stober process, using tetraethylorthosilicate (0.50 mL, 2.24 mmol), absolute ethanol (14.15 mL), and aqueous ammonia (9.0 M, 1.25 mL). The unfunctionalized Stober particles were washed by centrifugation in absolute ethanol. The supernatant was removed, and the pellet was re-suspended in absolute ethanol.

Figure 8A:
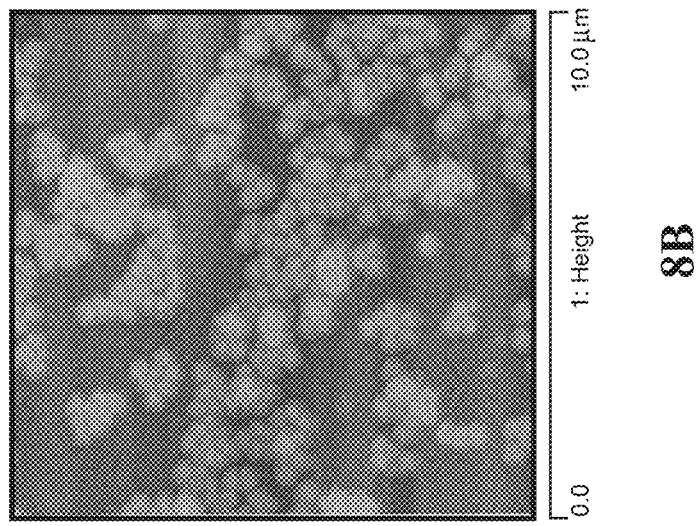
FIGS. 8A-8B show Atomic Force Microscope (AFM) images of (A) unfunctionalized (UF) nanosilica Stober particles, and (B) nanosilica Stober particles functionalized using compound 4 (F-Compound 4), in accordance with an embodiment of the present invention.
Figure 8B:
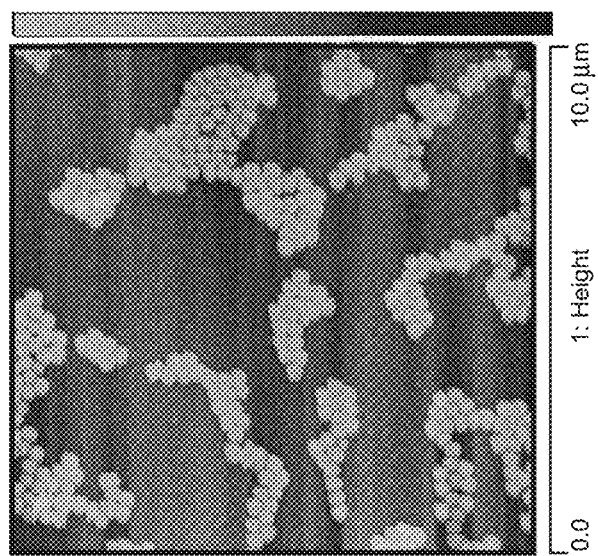
Figure 9:
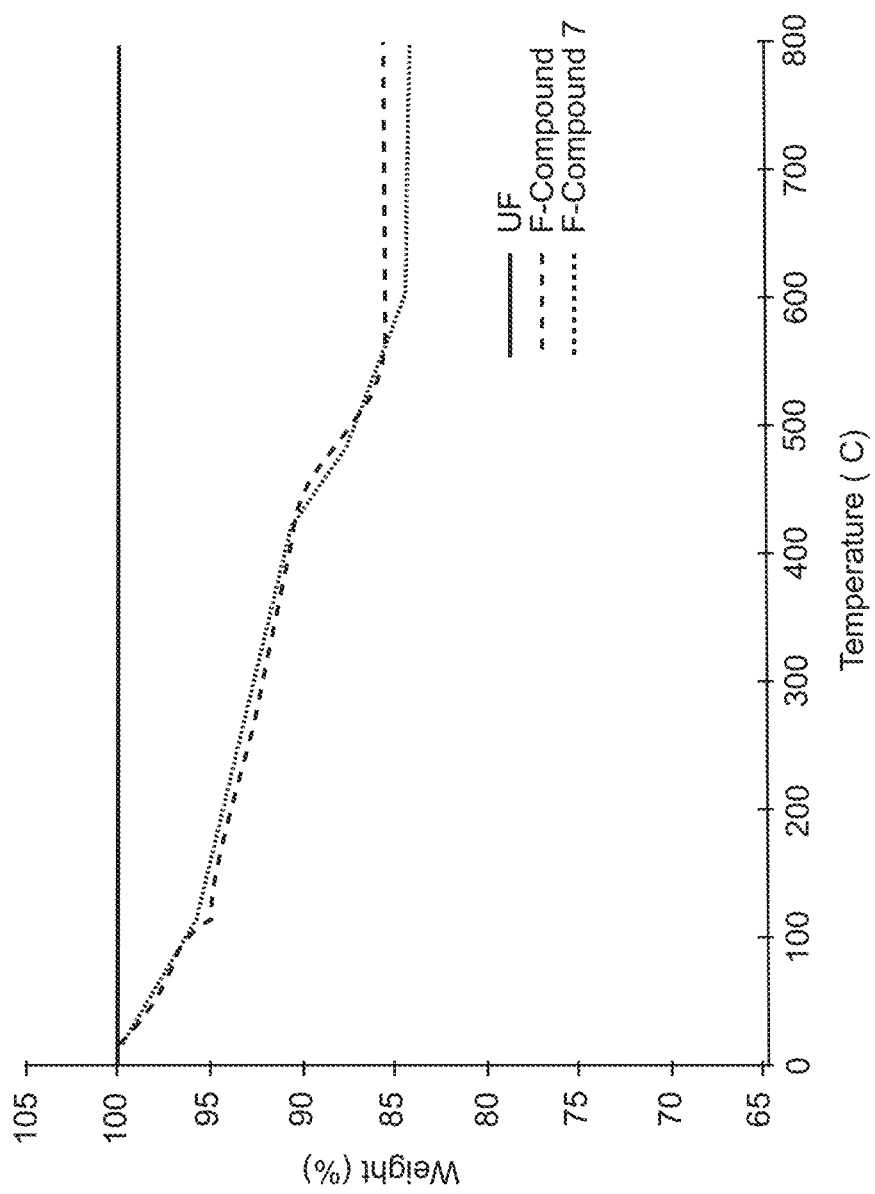
FIG. 9 is an overlay of thermogravimetric analysis (TGA) curves for unfunctionalized (UF) nanosilica Stober particles, nanosilica Stober particles functionalized using compound 4 (F-Compound 4), and nanosilica Stober particles functionalized using compound 7 (F-Compound 7).

The unfunctionalized washed Stober particles (5 mL) were added to a scintillation vial, equipped with a stir bar. To this stirred solution was added acetic acid (1.75 M, 0.20 mL), absolute ethanol (5 mL), and Compound 4 (0.50 g, 0.96 mmol). The vial was sealed and the suspension was stirred at room temperature overnight. The functionalized particles were washed by centrifugation in absolute ethanol. The supernatant was removed and the pellet was re-suspended in absolute ethanol. The functionalized Stober particles (F-Compound 4) were dried under reduced pressure and characterized by AFM and TGA (see FIGS. 8 and 9, respectively).

The unfunctionalized dried Stober particles (0.10 g) were added to a scintillation vial, equipped with a stir bar. To this stirred solution was added triethylamine (0.50 mL, 3.61 mmol), toluene (2.50 mL), and Compound 7 (1.00 g, 2.22 mmol). The vial was sealed and the suspension was stirred at room temperature overnight. The functionalized Stober particles were washed by centrifugation in absolute ethanol. The supernatant was removed and the pellet was re-suspended in absolute ethanol. The functionalized particles (F-Compound 7) were dried under reduced pressure and characterized by TGA (see FIG. 9).

Example 27

An aerogel was prepared utilizing Compound 16. Initially a catalytic solution (0.5 M NH$_4$F, 3.3 M NH$_4$OH) was prepared. Next, a solution containing Compound 16 (0.56 g, 0.68 mmol), absolute ethanol (2.75 mL), and tetraethylorthosilicate (1.34 mL, 6.00 mmol) was prepared in a 50 mL beaker. In a separate 50 mL beaker a second solution consisting of distilled water (2.1 mL), absolute ethanol (2.75 mL), 1,1,1,3,3,3-hexafluoro-2-propanol, and the catalytic solution (0.04 mL) was prepared. With stirring, this solution was added to the first beaker. The solution was poured into molds and allowed to gel for 72 hours. The gel was then allowed to age for 72 hours in absolute ethanol. The gels were placed in a critical point drying apparatus and supercritically dried using $CO_2$ (37° C., 8.3 MPa).

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method for synthesizing fluorinated cyclopentene moiety, comprising:

reacting perfluorocyclopentene and an unsaturated alcohol or an unsaturated thiol having an alkene or alkyne functional group; and performing a hydrosilylation of the alkene or the alkyne functional group with a silane.

2. The method of claim 1, wherein the hydrosilylation includes a platinum catalyst.

3. The method of claim 1, wherein the reacting perfluorocyclopentene and the unsaturated alcohol or the unsaturated thiol is performed in presence of a base.

4. The method of claim 3, wherein the base is selected from an amine, a bicarbonate, or a carbonate.

5. The method of claim 1, wherein the silane is selected from the group consisting of a mono-alkoxysilane ($R^4_2(R^3O)SiH$), a di-alkoxysilane, ($R^4(R^3O)_2SiH$), a tri-alkoxysilane (($R^3O)_3SiH$), or a chlorosilane, wherein $R^3$ and $R^4$ are selected from the group consisting of C1 to C10 alkyl, cycloalkyl, and aryl groups.

* * * * *